United States Patent [19]

Allway

[11] Patent Number: 5,460,925
[45] Date of Patent: Oct. 24, 1995

[54] PHOTOGRAPHIC COLOR COUPLERS AND PHOTOGRAPHIC MATERIALS CONTAINING THEM

[75] Inventor: Philip A. Allway, Watford, United Kingdom

[73] Assignee: Eastman Kodak Company, Rochester, N.Y.

[21] Appl. No.: 238,135

[22] Filed: May 4, 1994

[51] Int. Cl.⁶ .................................................. G03C 7/32
[52] U.S. Cl. .................... 430/379; 430/388; 430/389; 430/543; 430/558
[58] Field of Search .................................. 430/543, 558, 430/955, 388, 389, 379

[56] References Cited

U.S. PATENT DOCUMENTS

| | | | |
|---|---|---|---|
| 5,162,196 | 11/1992 | Sato et al. | 430/384 |
| 5,206,129 | 4/1993 | Sato et al. | 430/558 |
| 5,326,682 | 7/1994 | Yamakama | 430/558 |

FOREIGN PATENT DOCUMENTS

| | | | |
|---|---|---|---|
| 104423 | 4/1984 | European Pat. Off. . | |
| 149718 | 7/1981 | Germany . | |
| 279339 | 12/1987 | Japan | 430/558 |
| 1156748 | 6/1989 | Japan | 430/558 |
| 2304438 | 12/1990 | Japan | 430/558 |
| 93/07534 | 4/1993 | WIPO . | |

OTHER PUBLICATIONS

Synthesis Aug., 1992, Timothy Kearney et al., "Synthesis of Isatin 3–Oximes from 2–Nitroacetanilides" pp. 769–772.
Journal of Medicinal Chemistry, Paul W. Manley et al., "Structure Activity Studies of Potassium Channel Opening in Pinacidil–Type Cyanoguanidines, Nitroethenediamines, Thioureas, and Ureas" pp. 2327–2340.
Tetrahedron Report No. 107, S. Rajappa, "Preparation, Structure and Synthetic Potenial" pp. 1453–1480.

*Primary Examiner*—Lee C. Wright
*Attorney, Agent, or Firm*—Arthur E. Kluegel

[57] ABSTRACT

A photographic element comprises a support, at least one photosensitive silver halide layer and in or adjacent said silver halide layer a color coupler of one of the general formulas:

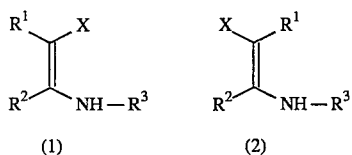

(1)      (2)

wherein
- $R^1$ is a group substantially without any electron-withdrawing capability,
- $R^2$ is a substituent not incompatible with the function of the compound,
- $R^3$ is an alkyl, aryl or heterocyclic group any of which may be substituted,
- provided that $R^1$ and $R^2$ or $R^1$ and $R^3$ may together form a cyclic group containing at least one heteroatom, and
- X is a coupling-off group.

The invention also provides a coupler composition, a dye composition, and a method of forming an image in the element of the invention.

9 Claims, 2 Drawing Sheets

PHOTOGRAPHIC COLOR COUPLERS AND PHOTOGRAPHIC MATERIALS CONTAINING THEM

FIELD OF THE INVENTION

This invention relates to photographic color couplers and in particular to a class of couplers.

BACKGROUND OF THE INVENTION

Color couplers are known to belong to a number of classes, for example magenta dye-forming couplers can be pyrazolones, pyrazolotriazoles and pyrazolobenzimidazoles while yellow dye-forming couplers can be acetanilides.

PROBLEM TO BE SOLVED BY THE INVENTION

There is always a need for new classes of couplers that have advantages over those already known to the art.

The present invention provides a new class of couplers capable of forming yellow dyes having good spectral characteristics such as maximum wavelength ($\lambda_{max}$), little unwanted absorption of green light and low continued coupling in the bleach.

SUMMARY OF THE INVENTION

According to the present invention there is provided a photographic element comprising a support, at least one photosensitive silver halide layer and in or adjacent said silver halide layer a color coupler of one of the general formulas:

$$\begin{array}{cc} R^1\diagdown\phantom{x}\diagup X & X\diagdown\phantom{x}\diagup R^1 \\ R^2\diagup\phantom{x}\diagdown NH-R^3 & R^2\diagup\phantom{x}\diagdown NH-R^3 \\ (1) & (2) \end{array}$$

wherein $R^1$ is a group substantially without any electron-withdrawing capability, $R^2$ is a substituent not incompatible with the function of the compound, $R^3$ is an alkyl, aryl or heterocyclic group any of which may be substituted, provided that $R^1$ and $R^2$ or $R^1$ and $R^3$ may together form a cyclic group containing at least one heteroatom, and X is a coupling-off group.

The invention also provides a coupler composition, a dye composition, and a method of forming an image in the element of the invention.

ADVANTAGEOUS EFFECT OF THE INVENTION

The present couplers form dyes on coupling with oxidised color developing agent, for example yellow dyes. The couplers, compared to presently used couplers, show less unwanted green absorption and display less continued coupling in the bleach.

DETAILED DESCRIPTION OF THE INVENTION

Figure 1:
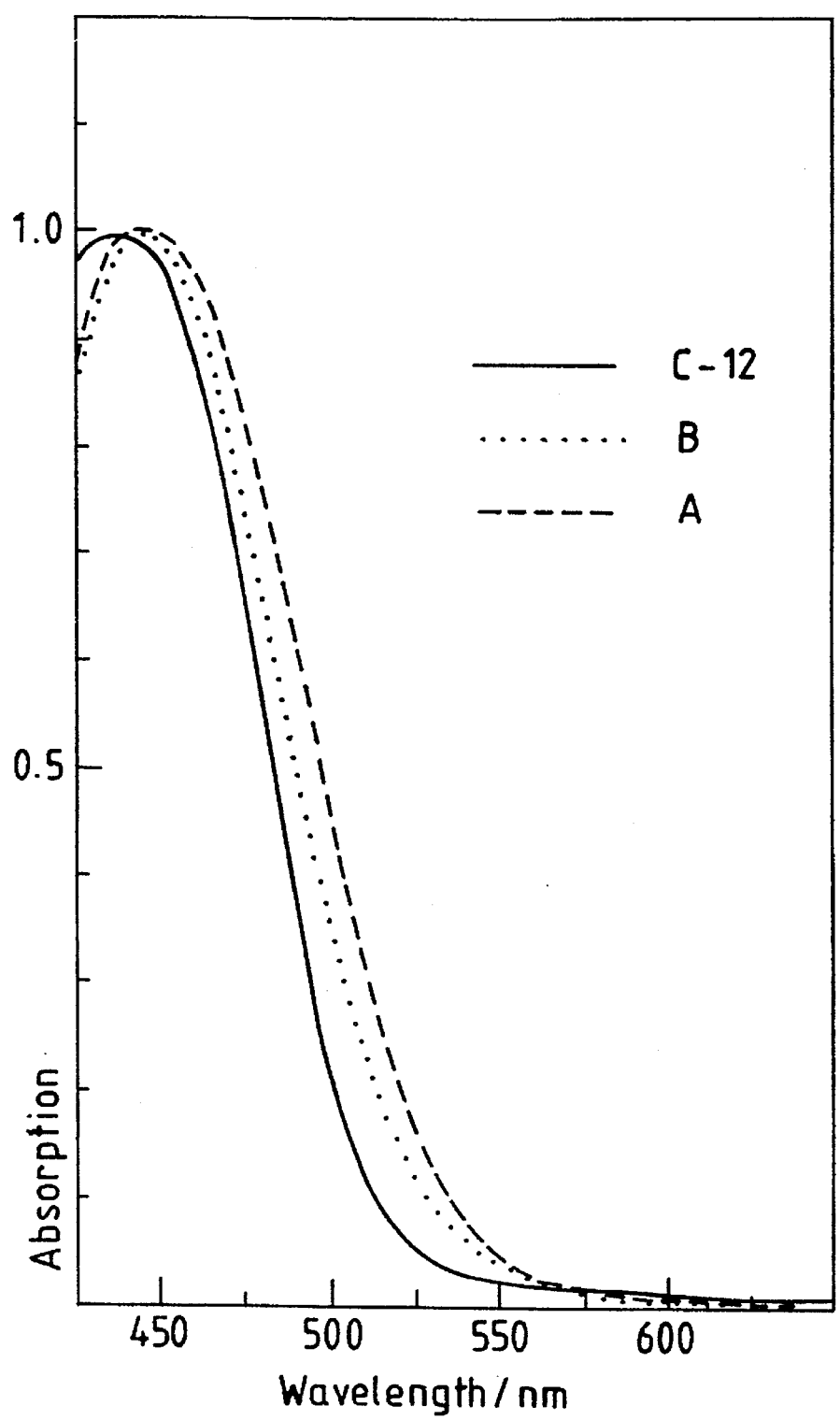
FIGS. 1 and 2 of the accompanying drawings are D LogE curves as described in Example 3 below

Examples of groups which $R^1$ may represent are hydrogen, or a substituted or unsubstituted aliphatic, a substituted or unsubstituted aryl, or substituted or unsubstituted heterocyclic group. The aliphatic group may be cyclic or acyclic, branched or unbranched, saturated or unsaturated. Examples of such groups are straight chain or branched alkyl or alkenyl groups of 1–20 carbon atoms, preferably 1–10 carbon atoms; cycloaliphatic groups of 3–20 carbon atoms; phenyl; or substituted phenyl.

Examples of groups which $R^2$ may represent are hydrogen, halogen (e.g. F, Cl or Br), thioalkyl, thioaryl, alkyl, substituted or unsubstituted aryl, substituted or unsubstituted heterocyclic, cyano, carbonamido, alkyloxy, aryloxy, alkyloxycarbonyl, alkylsulphoxyl, arylsulphoxyl, alkylsulphonyl, arylsulphonyl, amino, nitro, or a phosphorus atom substituted with a variety of hydrocarbon groups or an acyl group.

Examples of groups which $R^3$ may represent are substituted or unsubstituted aryl, substituted or unsubstituted heterocyclic, or an acyl group.

Representative substituents on such groups include alkyl, aryl, alkoxy, aryloxy, alkylthio, hydroxy, halogen, alkoxycarbonyl, aryloxycarbonyl, carboxy, acyl, acyloxy, amino, anilino, carbonamido, carbamoyl, alkylsulfonyl, arysulfonyl, sulfonamido, and sulfamyl groups wherein the substituents typically contain 1 to 40 carbon atoms. Such substituents can also be further substituted.

Coupling-off groups are well known in the art. Such groups can determine the equivalency of the coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, development acceleration or inhibition, bleach acceleration or inhibition, electron transfer facilitation, color correction and the like.

Examples of coupling-off groups include chloro, alkoxy, aryloxy (e.g. phenyloxy or 2-chloro-, 2,3,5-isopropyl-, 4-carboxy-, 4-carboxy-2-methylcarbonamido, 4-nitro-2-carbamoyl-phenyloxy), alkylthio, arylthio (e.g. phenylthio, or 2,3,5-isopropyl-phenylthio), heteroyloxy (e.g. pyridyloxy), sulfonyloxy, acyloxy, carboxy, acyl, heterocyclyl joined via a ring carbon or hetero atom in the heterocyclic nucleus, sulfonamido, mercaptotetrazole, mercaptopropionic acid, phosphonyloxy and arylazo (e.g. 4-hydroxy-, 4-hexadecyloxy-3-methoxy-4-methyl-2-hydroxy-, 4-methylsulphonyl- or 4-t-butytcarbonamidophenytthio). Nitro is a particularly preferred coupling-off group.

The group which splits off may provide a photographically useful compound. Many such groups are often known as photographically useful groups and they provide developer inhibitors, bleach accelerators, developer accelerators, antifoggants, competing couplers, etc. Many examples are listed in Research Disclosure Item 308119, December 1989 published by Kenneth Mason Publications, Emsworth, Hants, United Kingdom. Examples of such groups are shown in Table 1 below.

TABLE 1

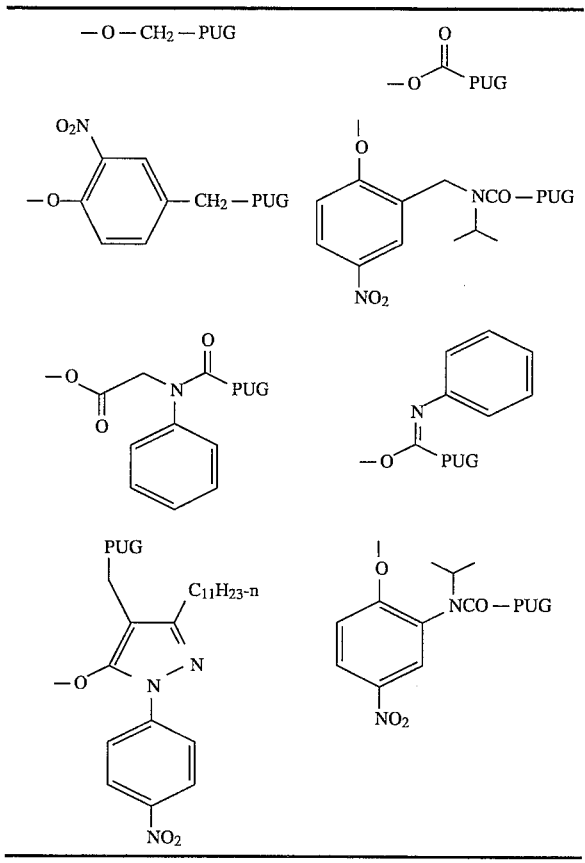

The couplers of this invention can be used in any of the ways and in any of the combinations in which couplers are used in the photographic art. Typically, the coupler is incorporated in a silver halide emulsion and the emulsion coated on a support to form part of a photographic element. Alternatively, the coupler can be incorporated at a location adjacent to the silver halide emulsion where, during development, the coupler will be in reactive association with development products such as oxidized color developing agent. Thus, as used herein, the term "associated" signifies that the coupler is in the silver halide emulsion layer or in an adjacent location where, during processing, the coupler is capable of reacting with silver halide development products.

In one embodiment of the present invention the couplers contain a ballasting group of such size and configuration to render the coupler non-diffusible in the photographic material. Such a group may form part of $R^1$ $R^2$ or $R^3$.

Representative ballast groups include substituted or unsubstituted alkyl or aryl groups containing 8 to 40 carbon atoms.

Examples of couplers of the present invention are listed in Table below.

TABLE 2

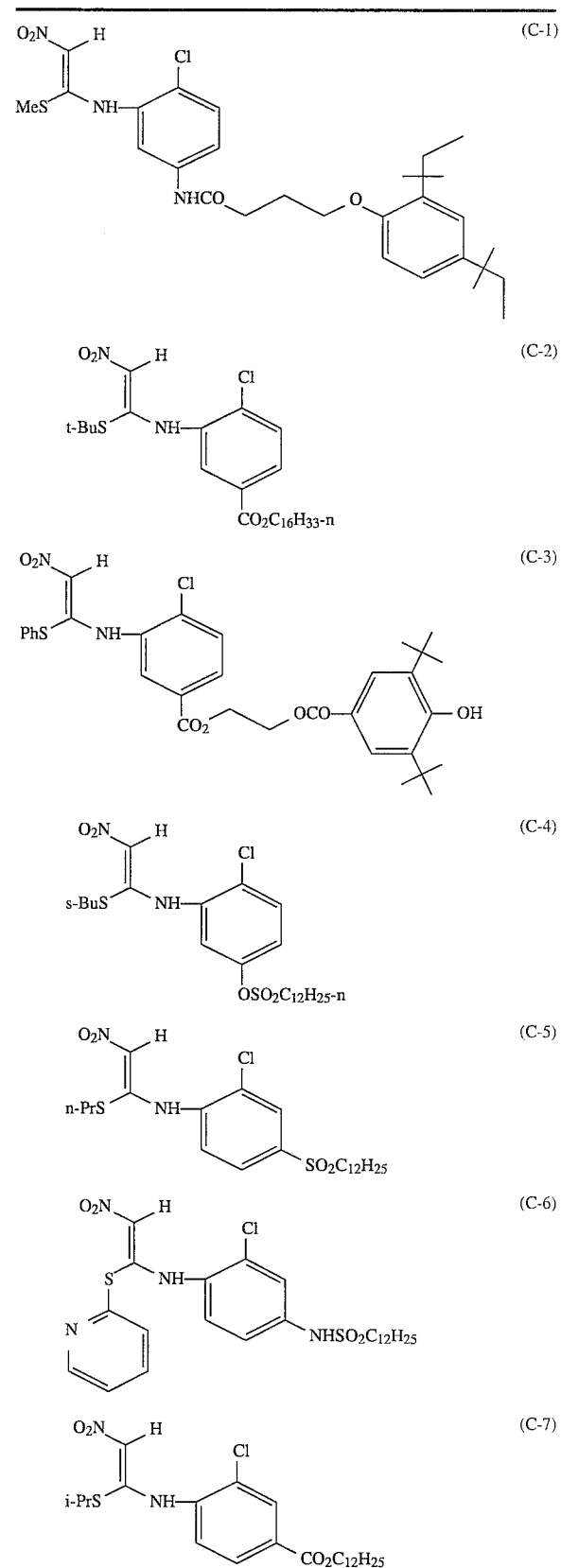

TABLE 2-continued
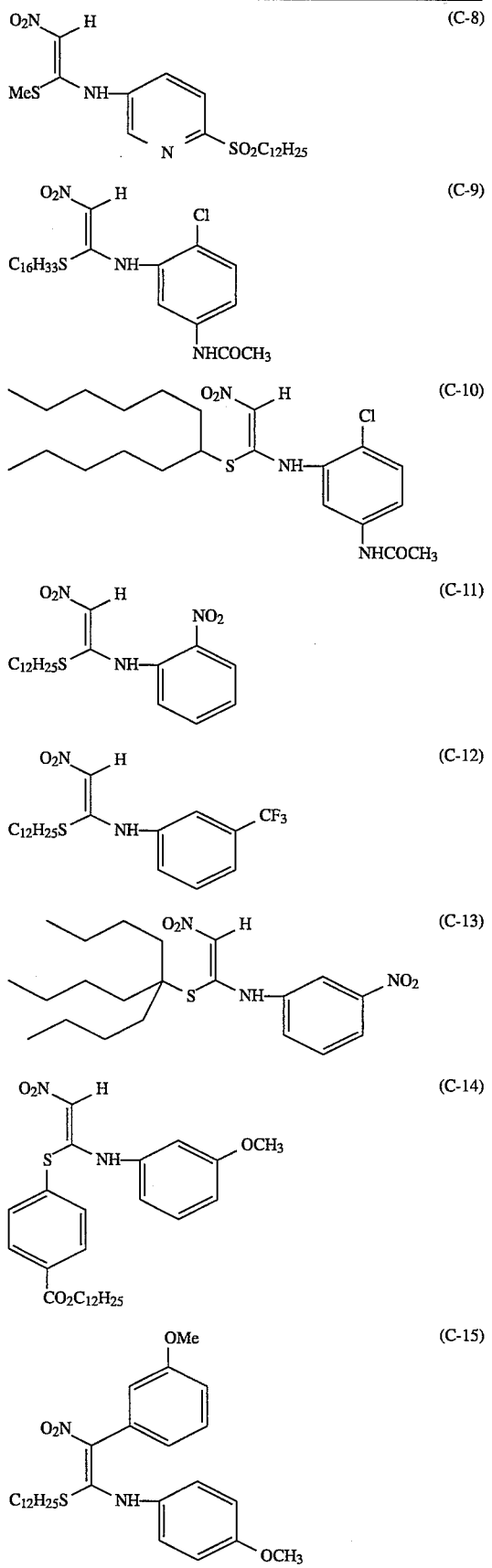
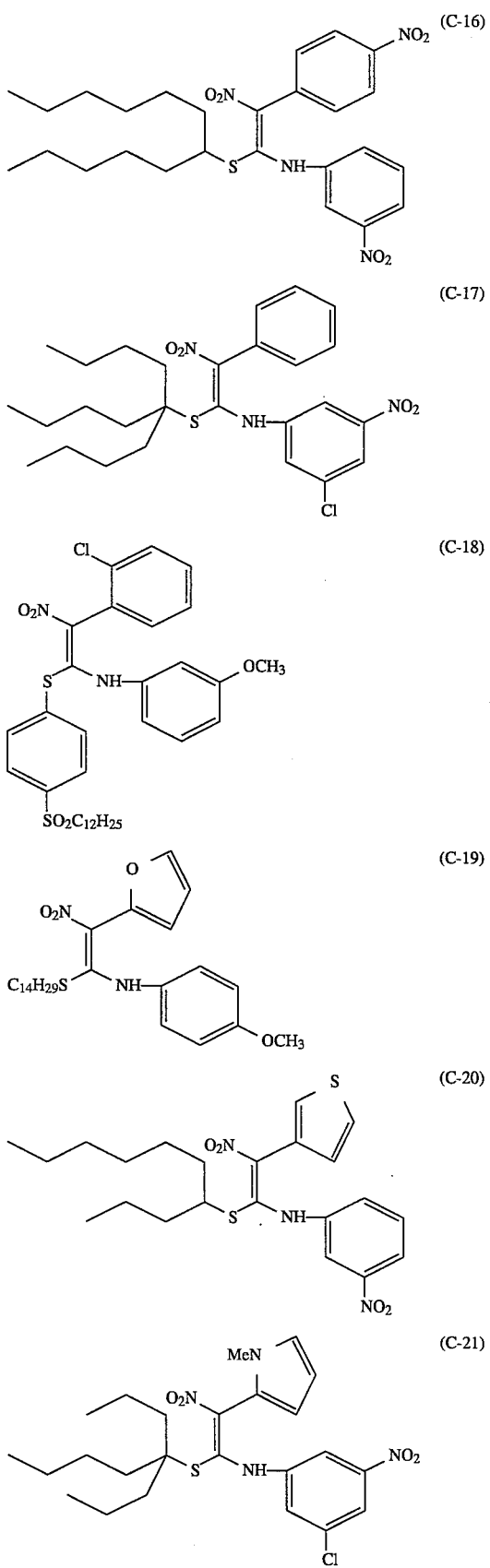

TABLE 2-continued
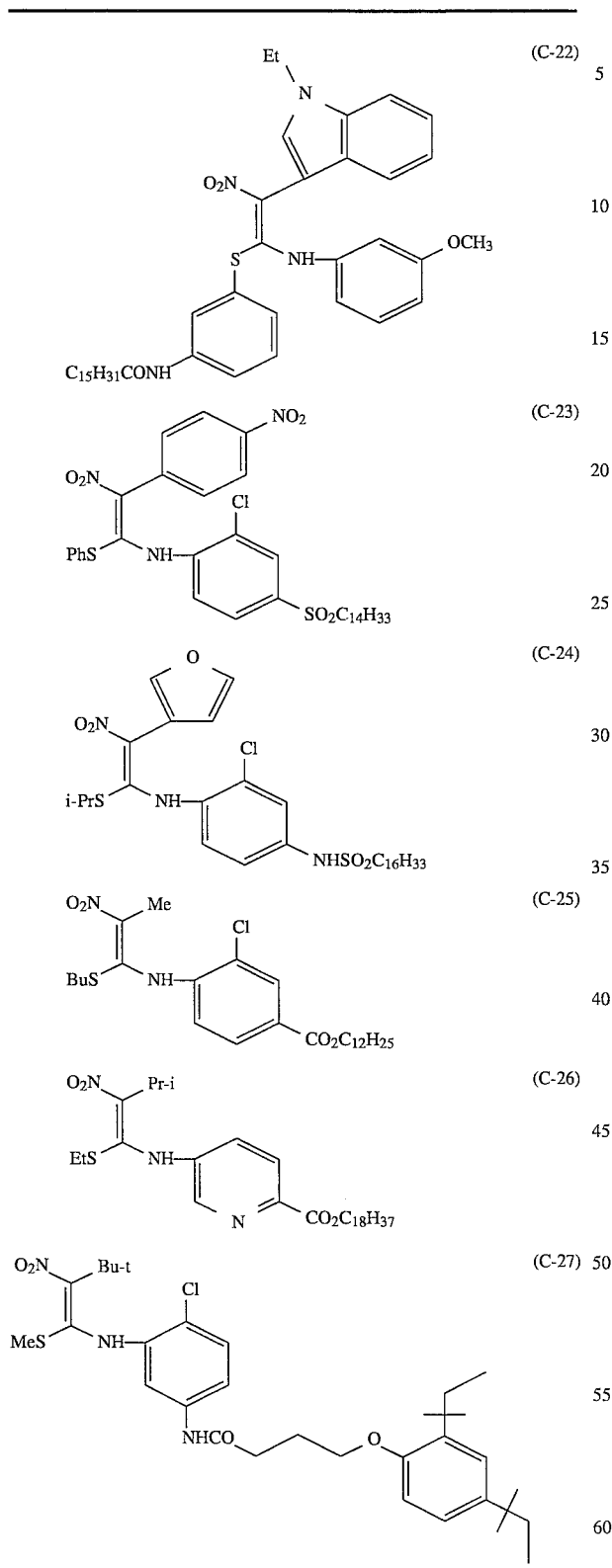
TABLE 2-continued
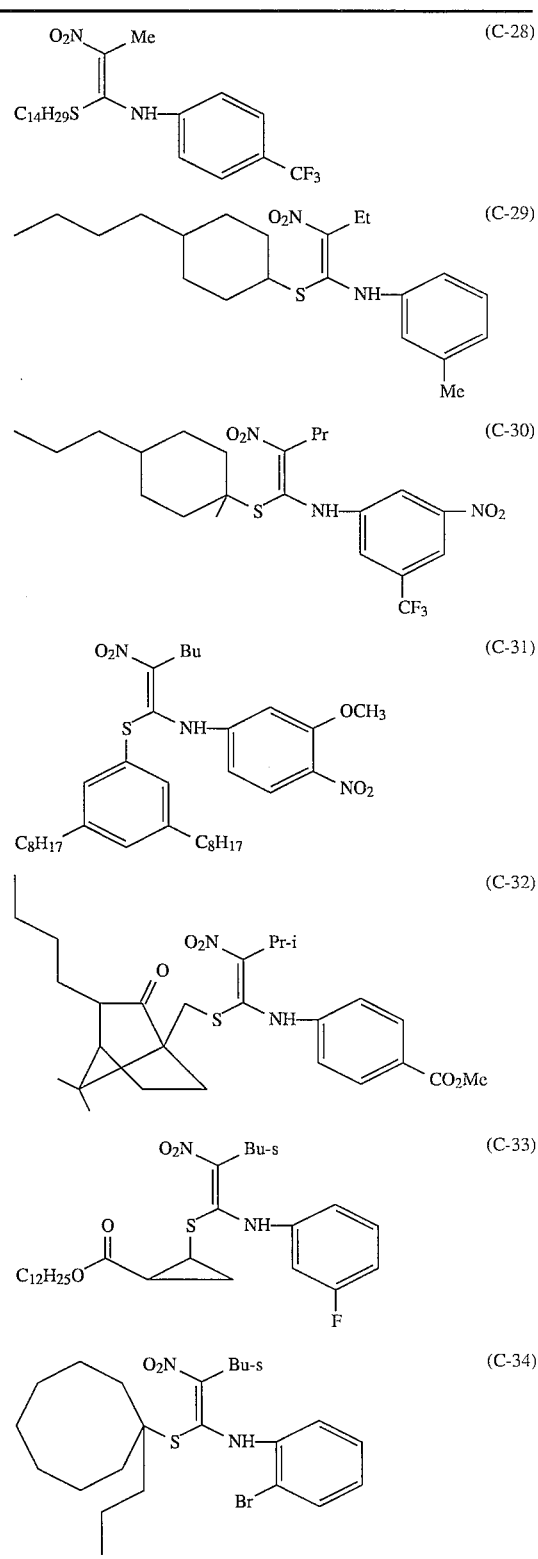

TABLE 2-continued
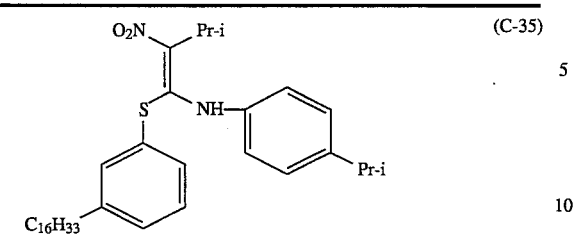 (C-35)
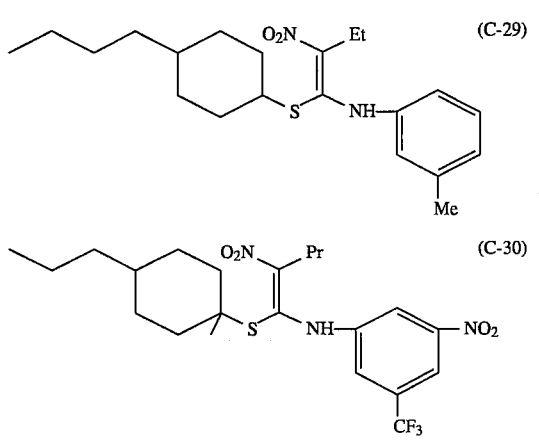 (C-29)
(C-30)
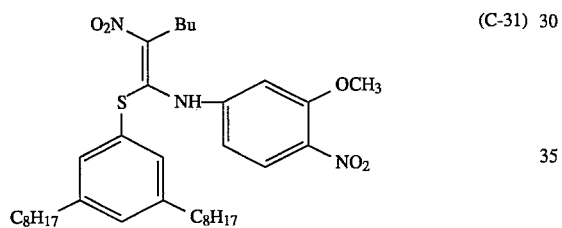 (C-31)
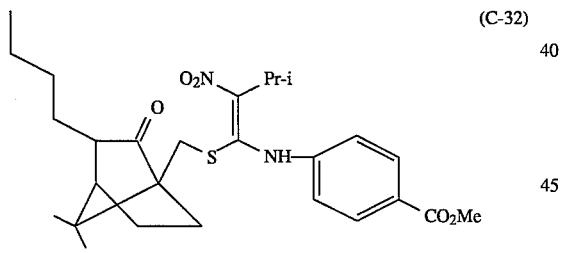 (C-32)
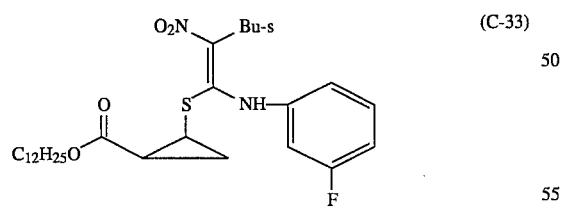 (C-33)
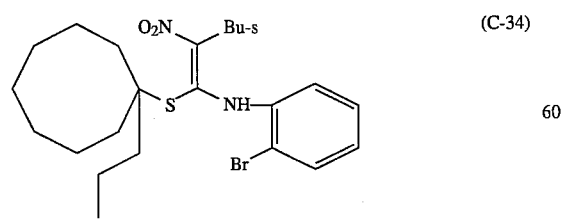 (C-34)
TABLE 2-continued
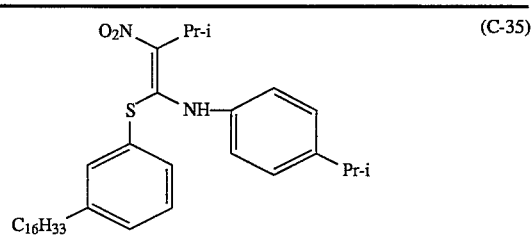 (C-35)
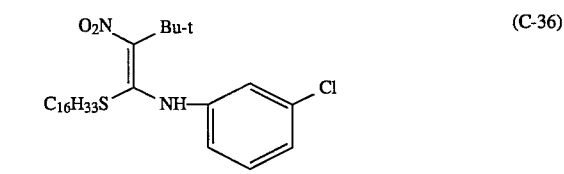 (C-36)
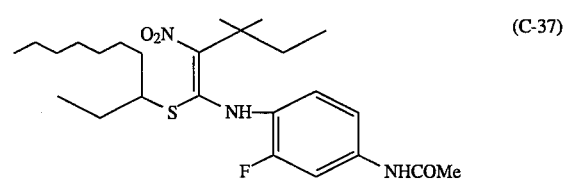 (C-37)
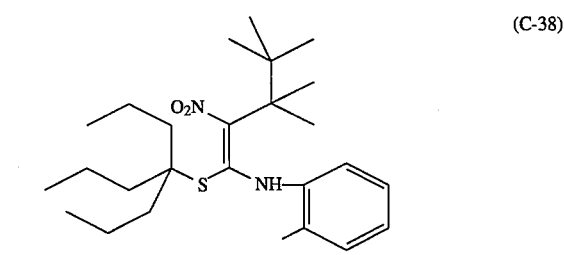 (C-38)
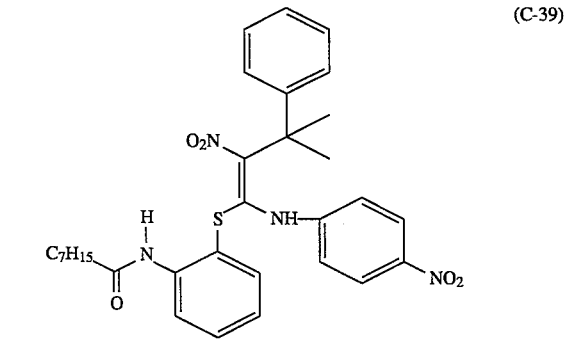 (C-39)
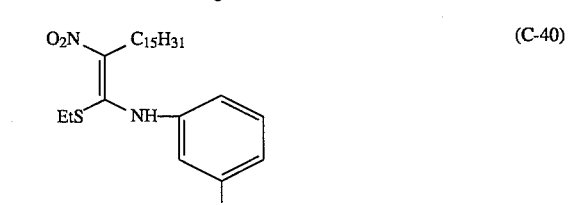 (C-40)
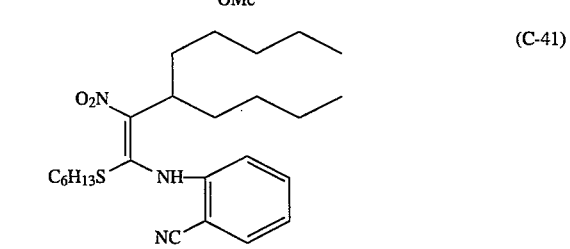 (C-41)

TABLE 2-continued
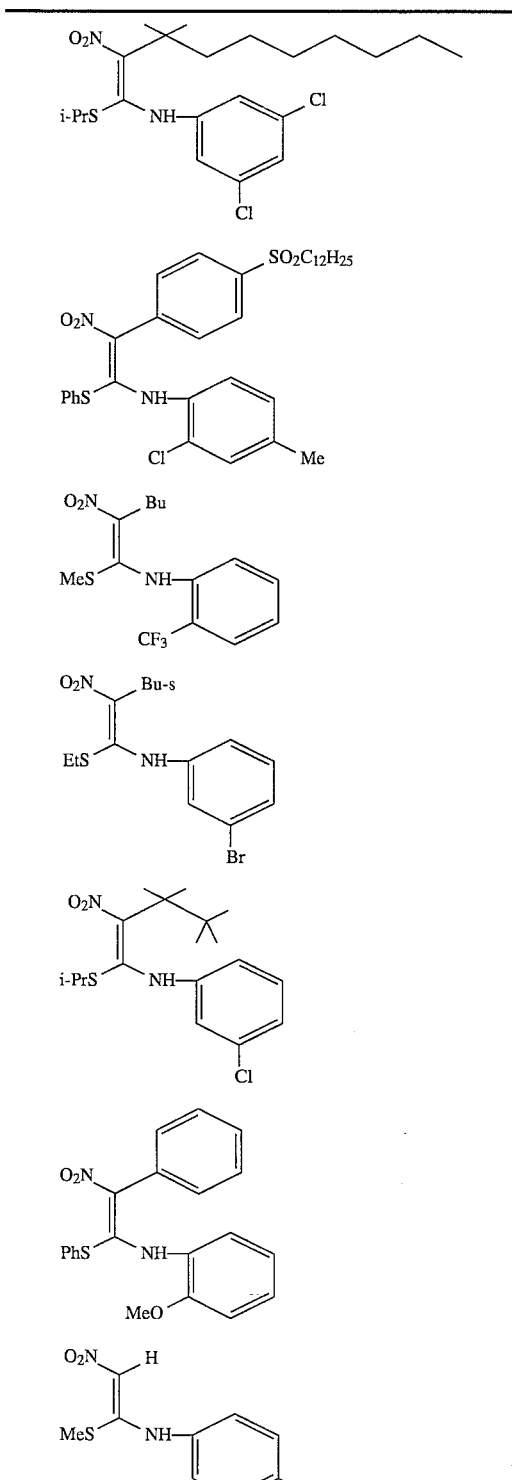
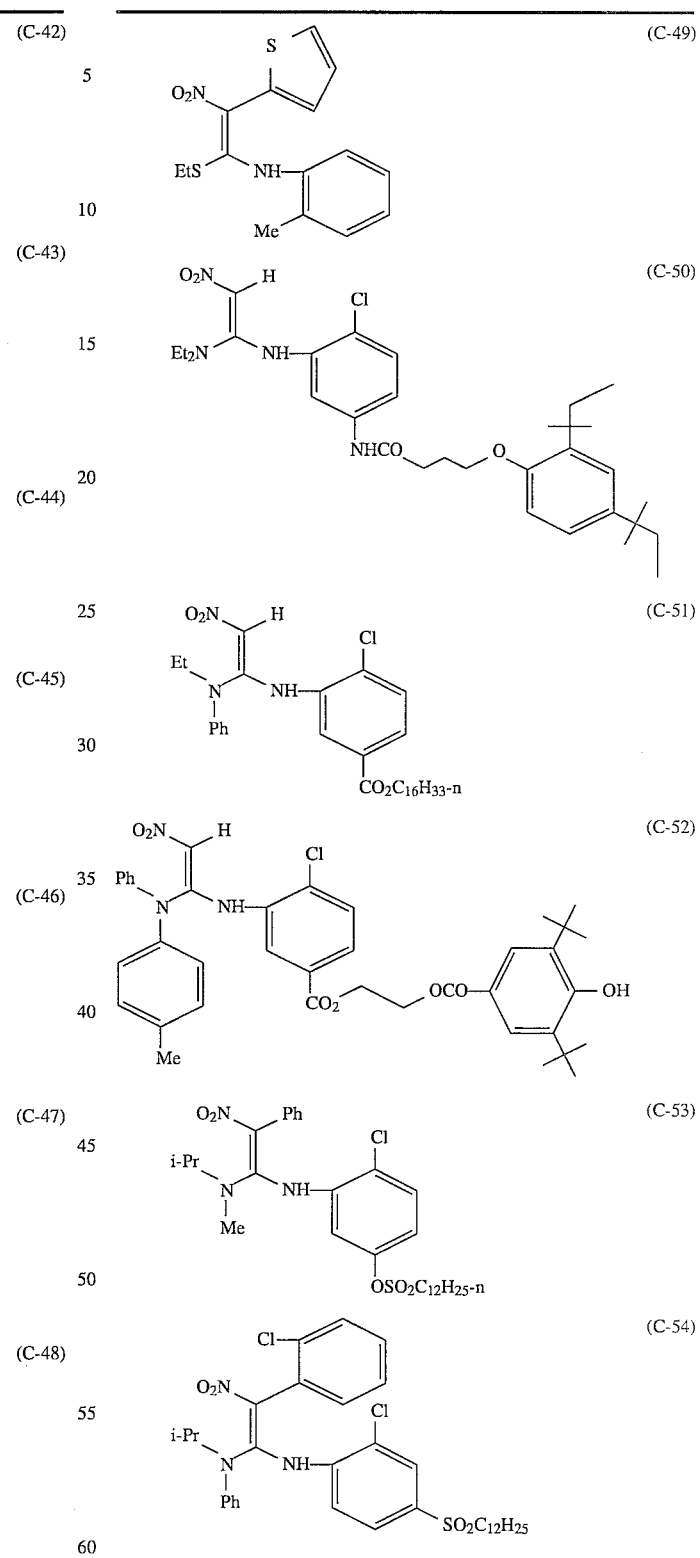

TABLE 2-continued
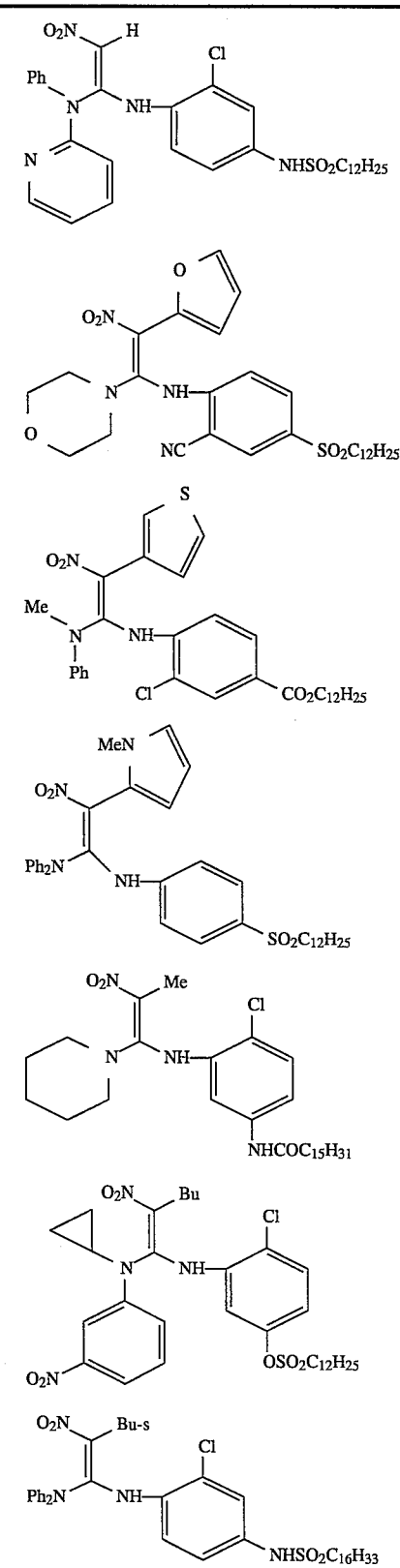
TABLE 2-continued
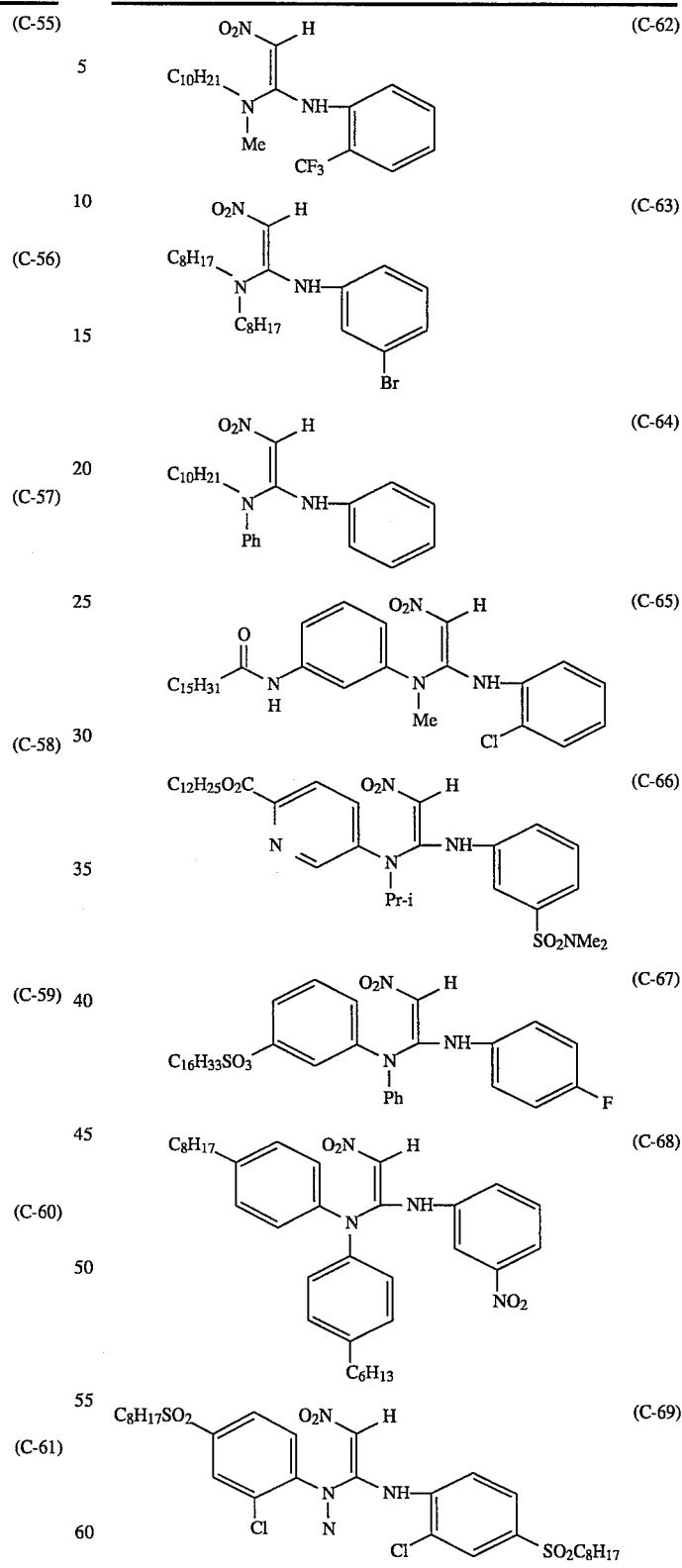

TABLE 2-continued
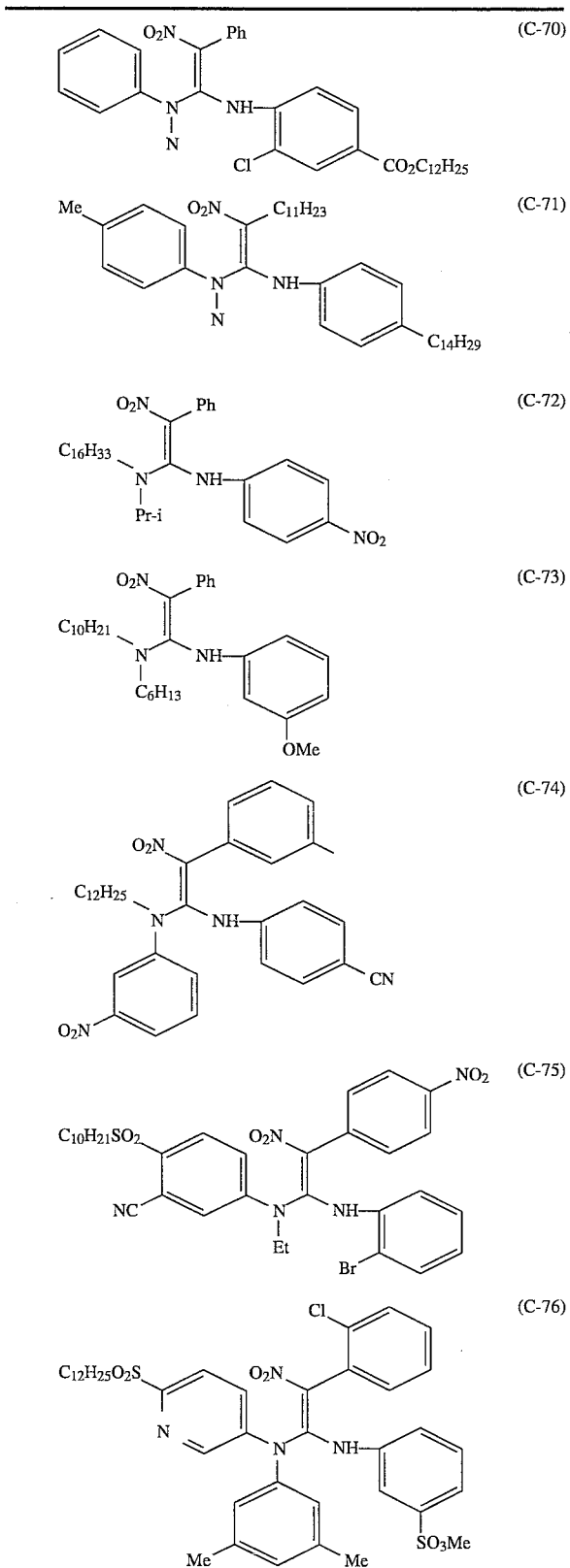
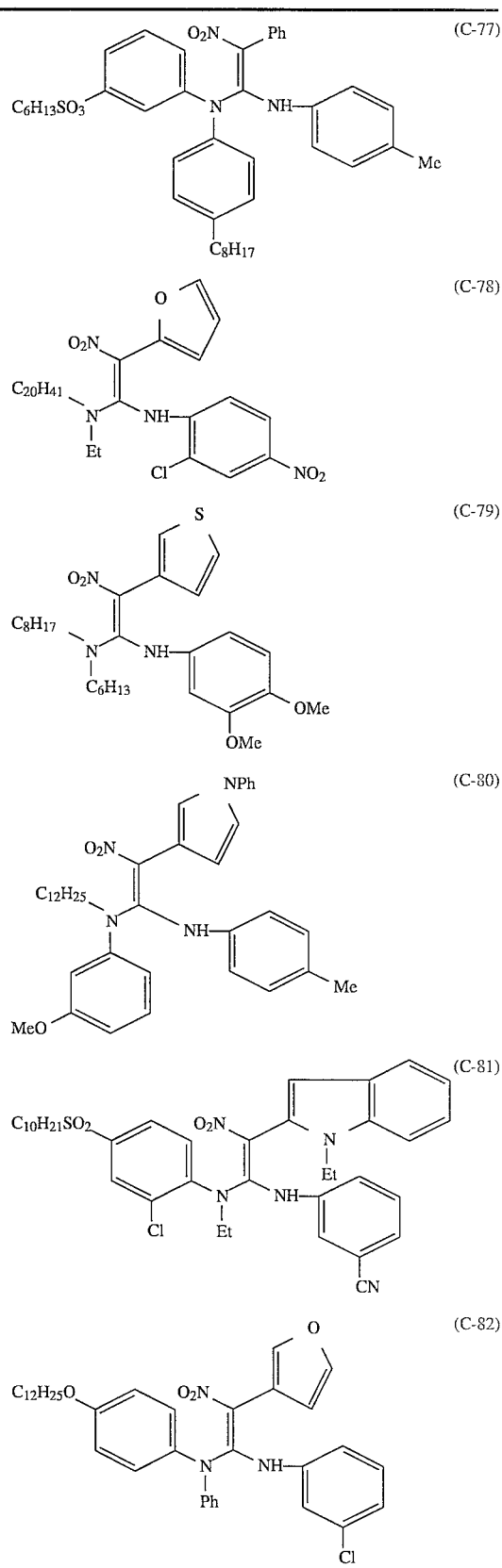

TABLE 2-continued
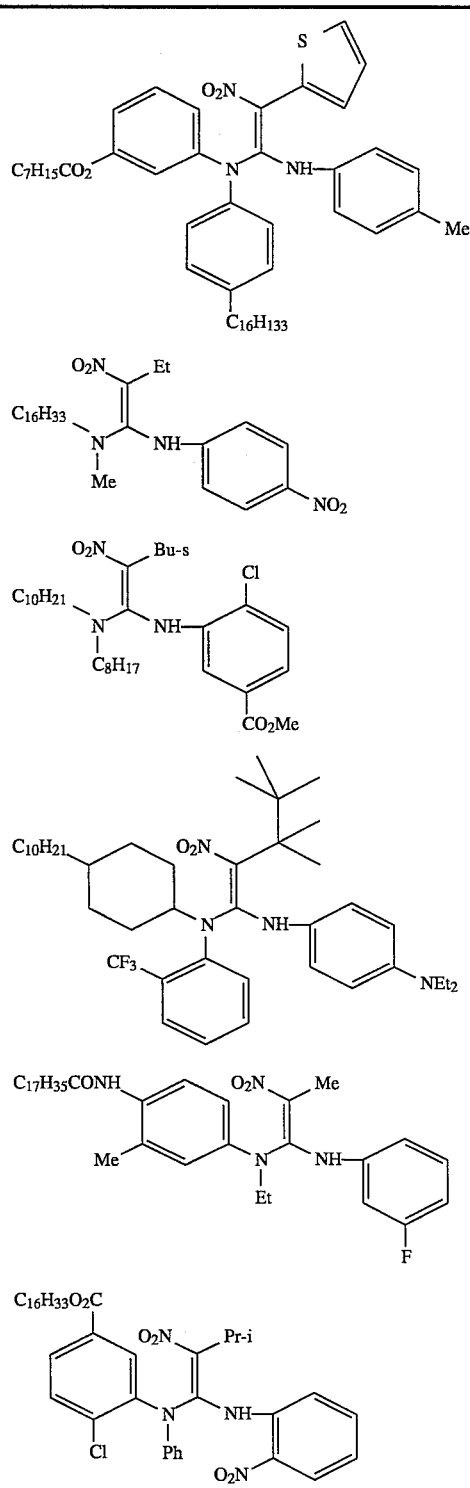
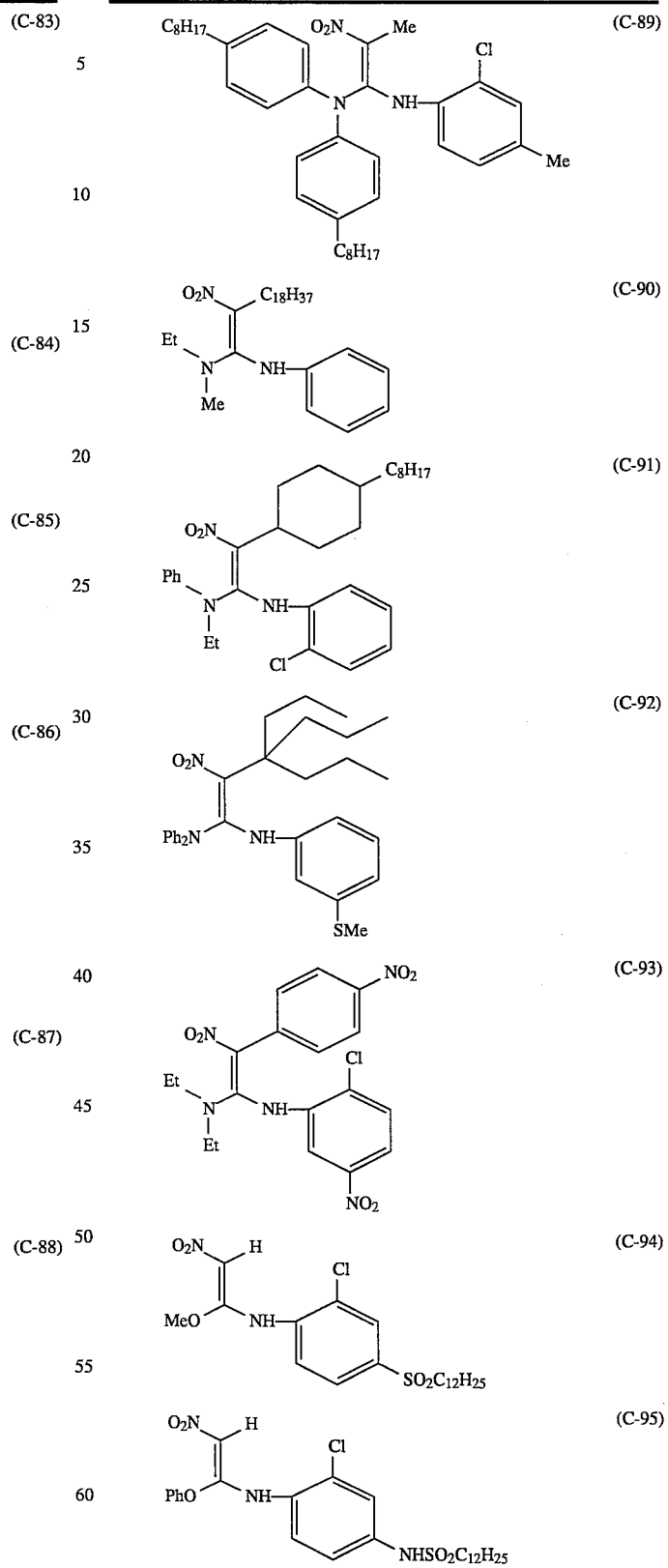

TABLE 2-continued
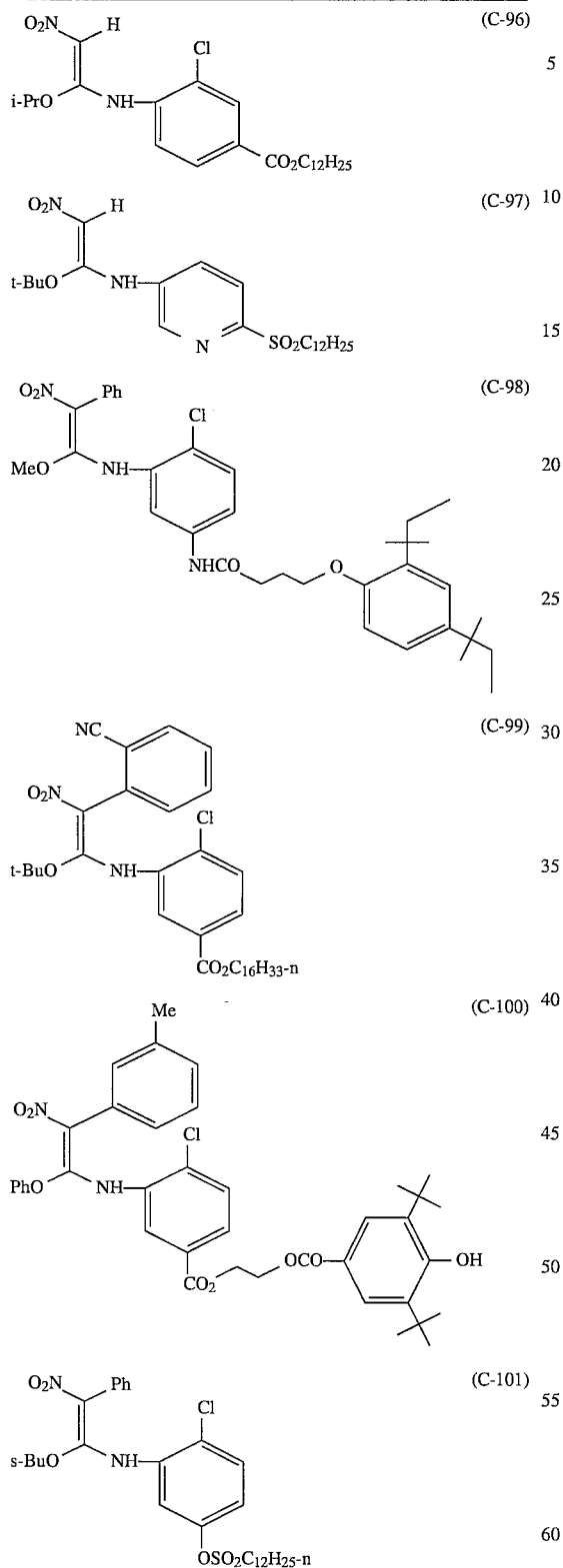
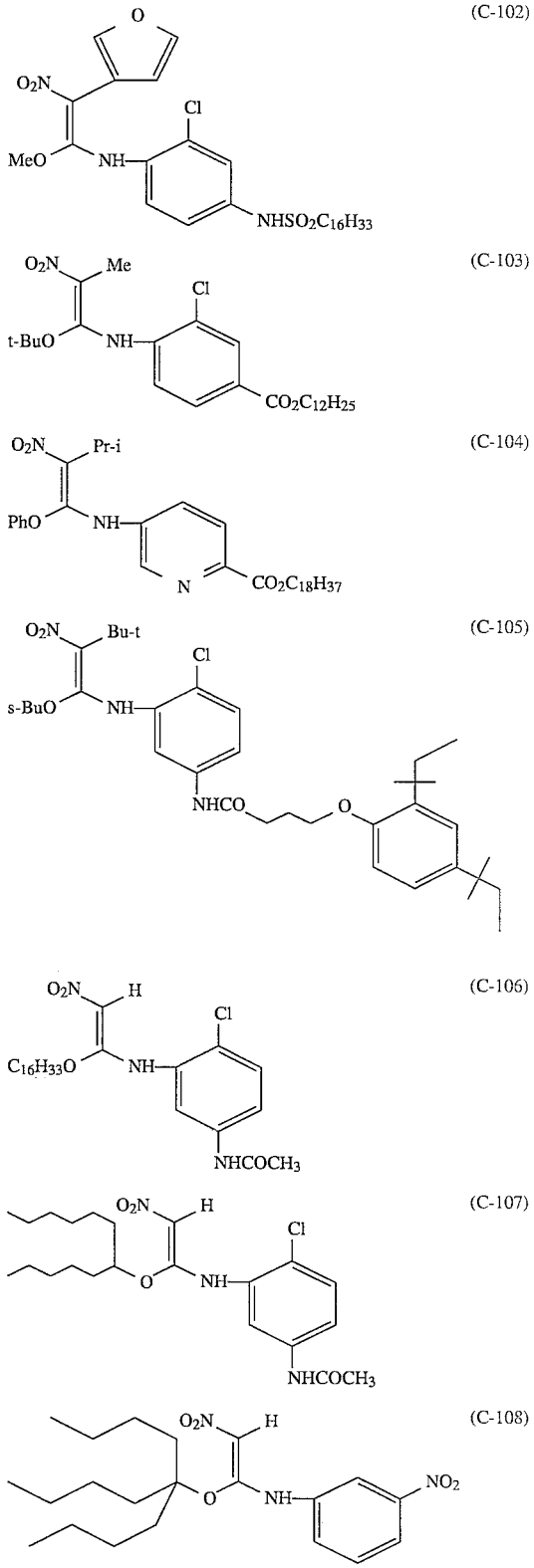

TABLE 2-continued
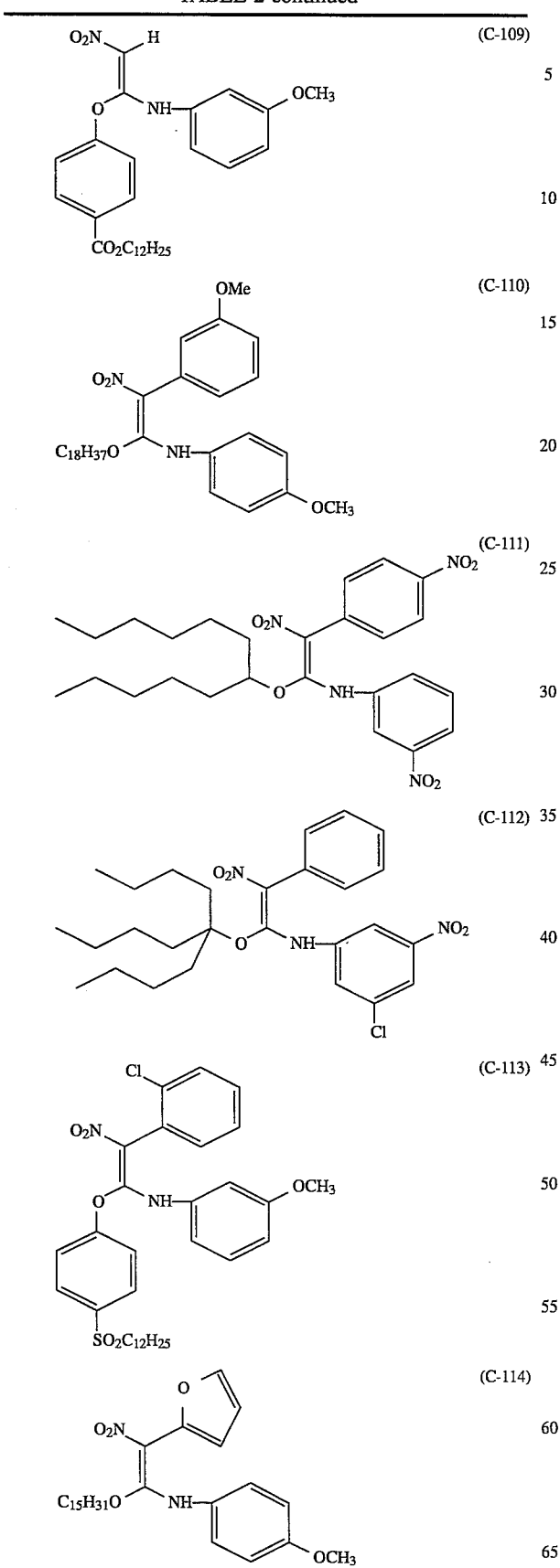
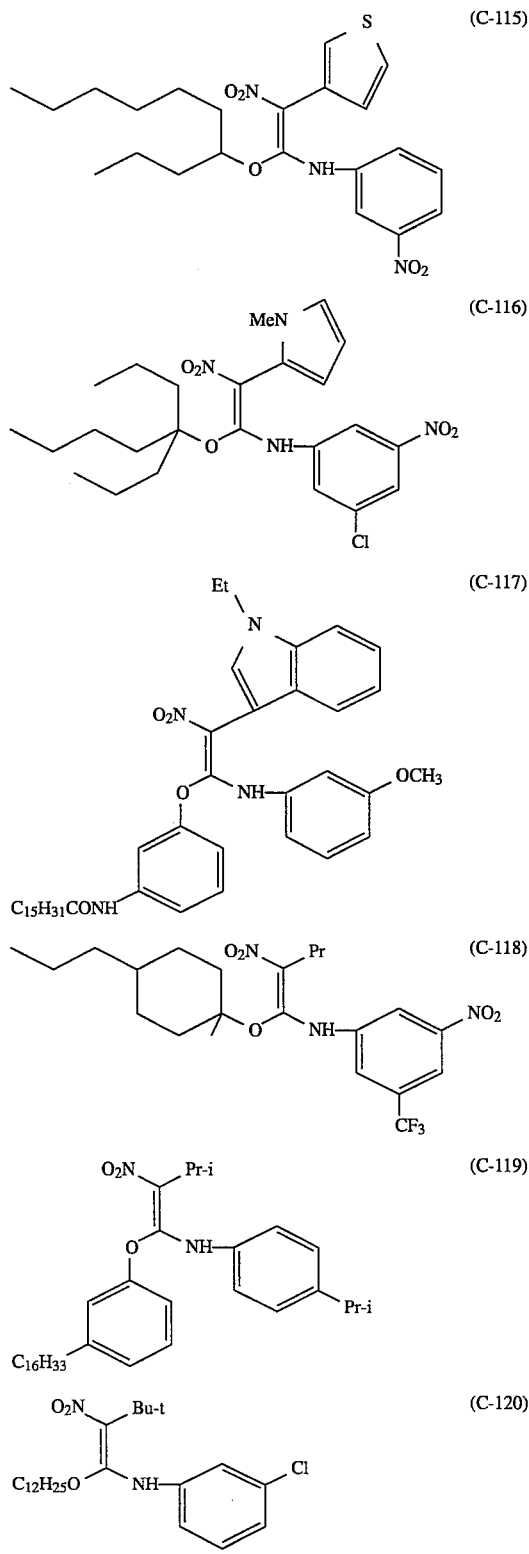

TABLE 2-continued
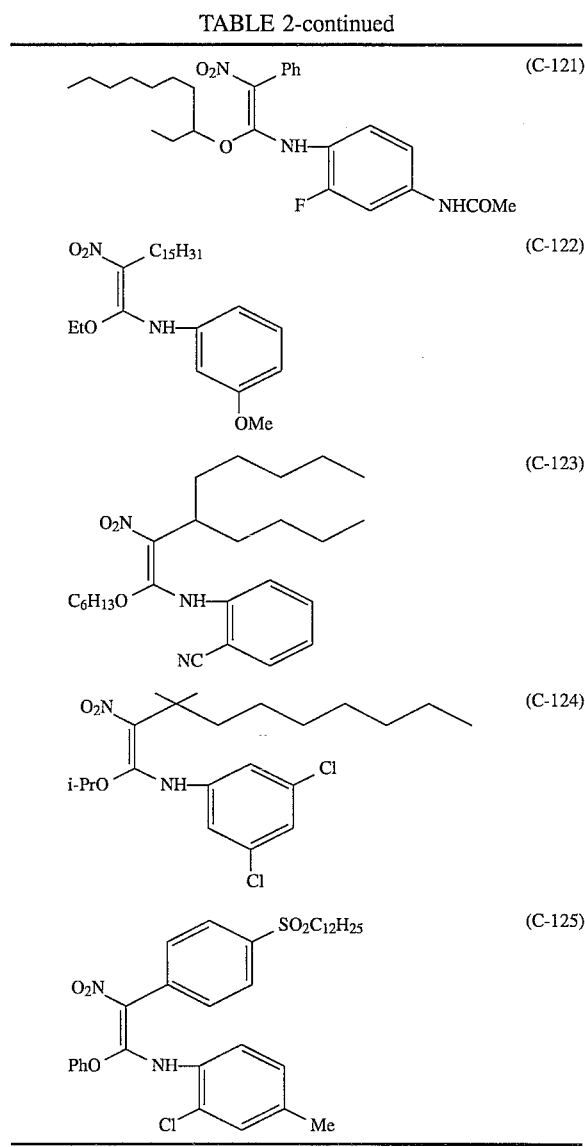
where X is:-
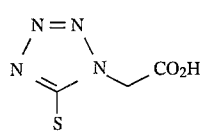 C-126
-continued
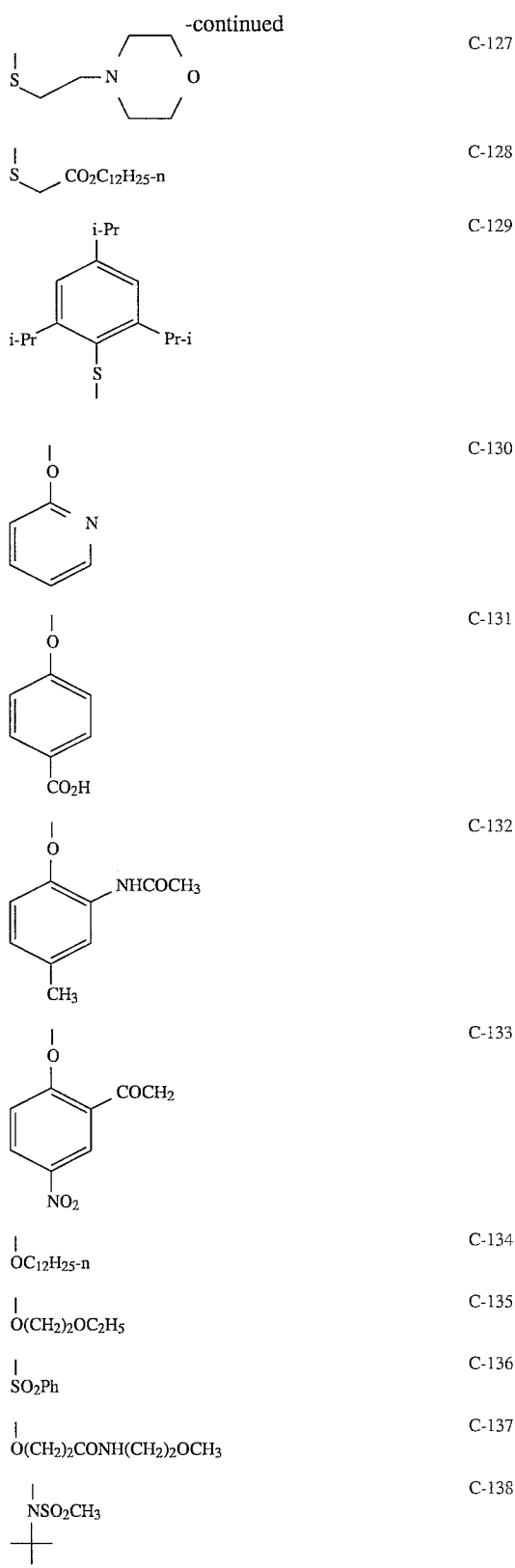

-continued

C-139 through C-146 (structures shown)

C-147 through C-154 (structures shown)

where X is:-

-continued

C-155: [structure: 2-methoxy-5-methyl-N-acetylaniline]

C-156: [structure: 2-methoxy-5-nitrophenyl with COCH₂ group]

C-157: –OC₁₂H₂₅-n

C-158: –O(CH₂)₂OC₂H₅

C-159: –SO₂Ph

C-160: –O(CH₂)₂CONH(CH₂)₂OCH₃

C-161: –NSO₂CH₃ (on t-butyl)

C-162: [structure: uracil derivative with methyl]

C-163: [structure: 1-methyl-2-pyridone]

C-164: [structure: N-benzyl hydantoin-type ring]

C-165: [structure: N=N-phenyl-4-OH]

C-166: [structure: N=N-phenyl-3-OCH₃-4-OC₁₂H₂₅-n]

-continued

C-167: [structure: N=N-phenyl with OH and CH₃]

C-168: [structure: naphthol bis-azo with NaO₃S, SO₃Na, NHCOCH₃, OH and p-methoxyphenyl group]

C-169: [structure: N=N-phenyl-4-SO₂CH₃]

C-170: [structure: N=N-phenyl-4-NHCOBu-t]

C-171: [structure: tetrazole-5-thione N-ethyl, S-methyl]

—

[structure: 4-SO₂C₁₂H₂₅-phenyl with X=C and PhS–C(NH-2-Cl-4-Me-phenyl)]

where X is:-

C-172: [structure: tetrazole-5-thione with N-CH₂CO₂H and S-methyl]

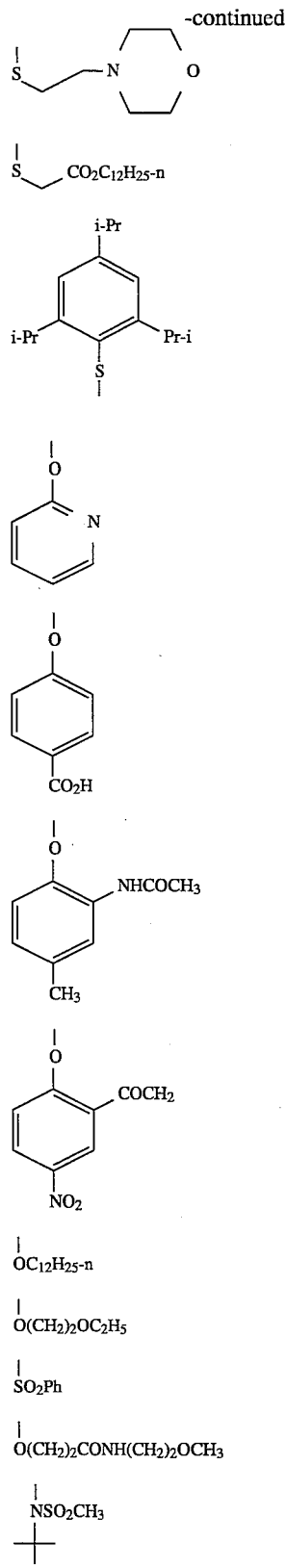
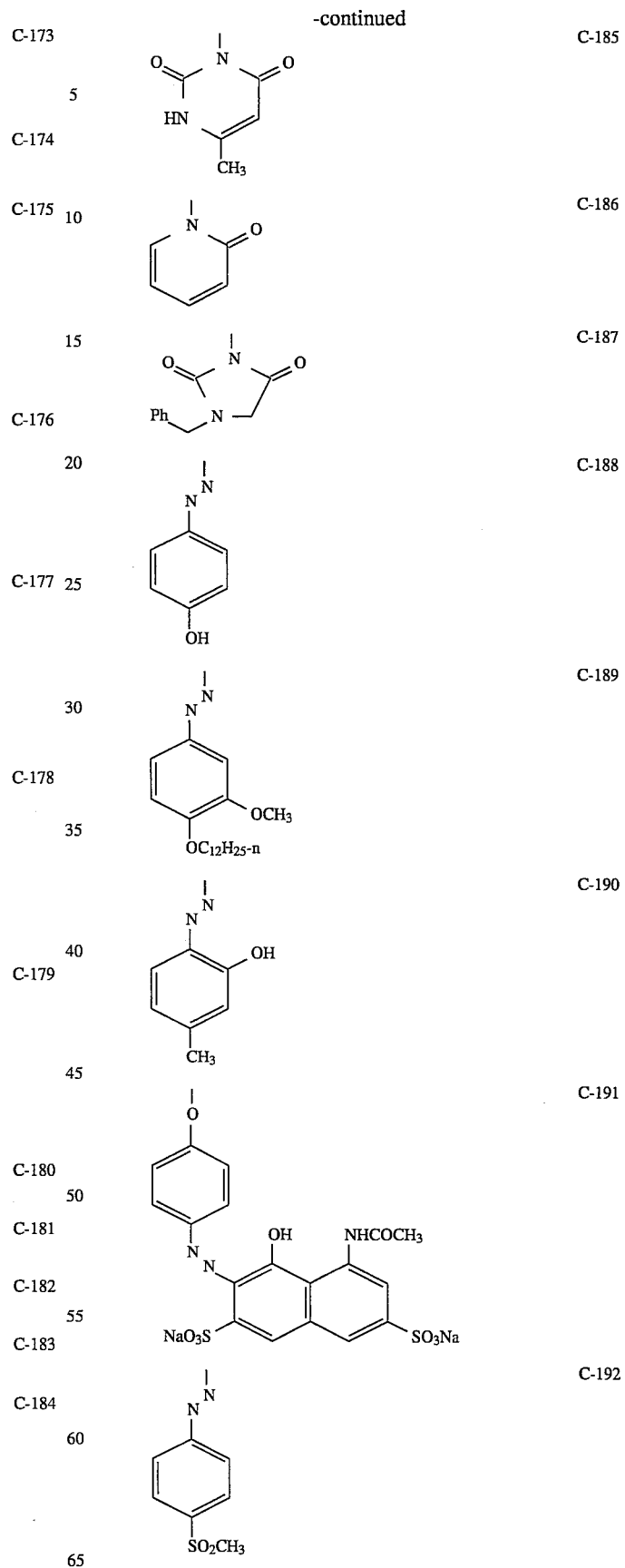

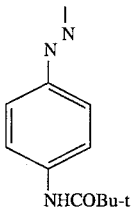
C-193
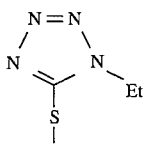
C-194
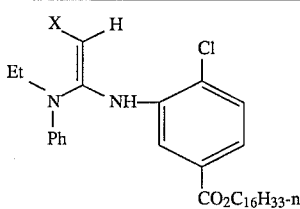
where X is:-
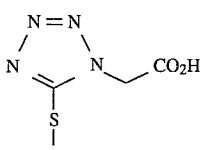
C-195
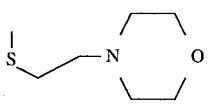
C-196
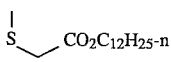
C-197
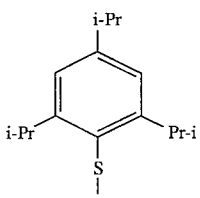
C-198
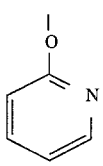
C-199
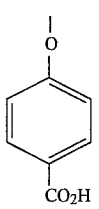
C-200
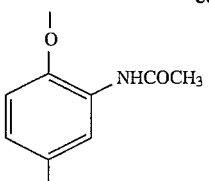
C-201
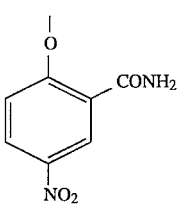
C-202
$OC_{12}H_{25}$-n
C-204
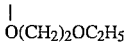
$O(CH_2)_2OC_2H_5$
C-205
$SO_2Ph$
C-206
$O(CH_2)_2CONH(CH_2)_2OCH_3$
C-207
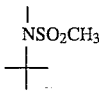
$NSO_2CH_3$
C-208
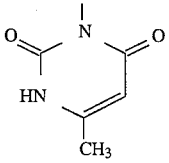
C-209
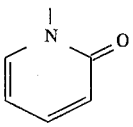
C-210
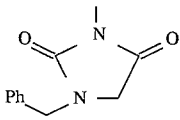
C-211
C-212
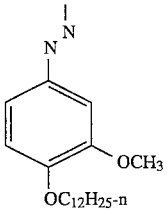
C-213

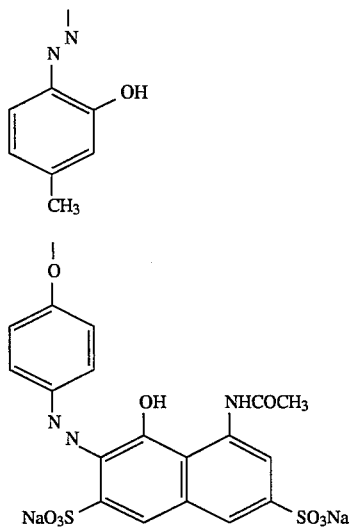

-continued
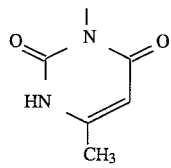
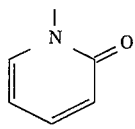
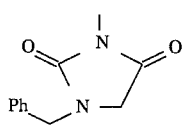
C-232
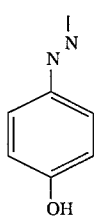
C-233
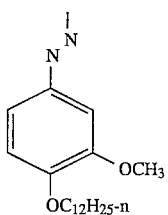
C-234
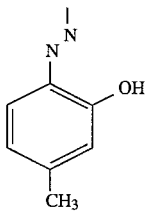
C-235
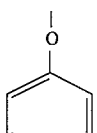
C-236
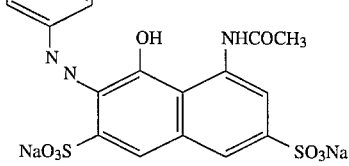
C-237
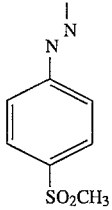
C-238
C-239
-continued
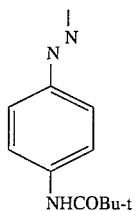
NHCOBu-t
C-240
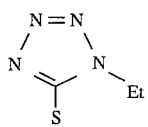
C-241
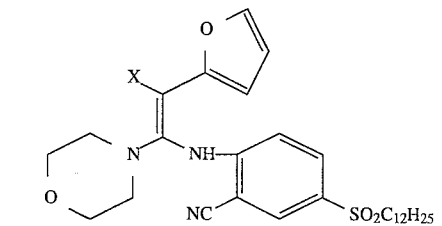
where X is:-
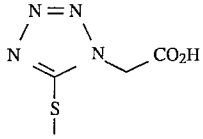
C-242
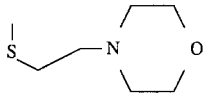
C-243
S CO₂C₁₂H₂₅-n
C-244
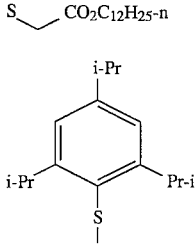
C-245
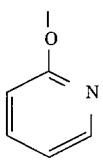
C-246

-continued
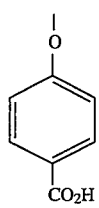
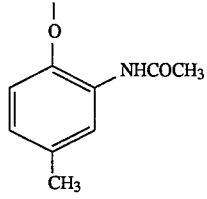
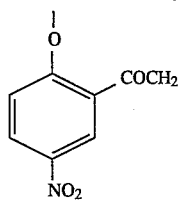
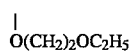
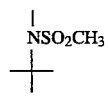
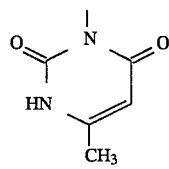
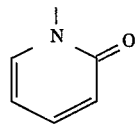
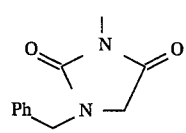
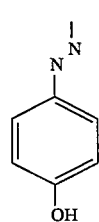
-continued
C-247
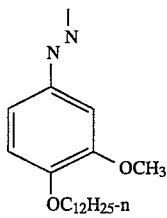
C-248
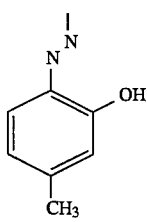
C-249
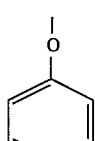
C-250
C-251
C-252
C-252
C-253
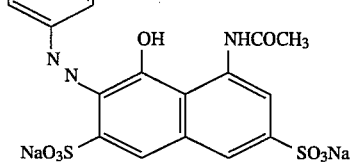
C-254
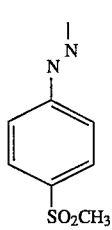
C-255
C-256
C-257
C-258
C-259
C-260
C-261
C-262
C-263
where X is:-

-continued
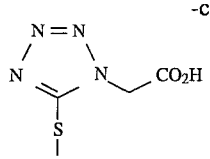
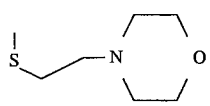
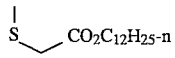
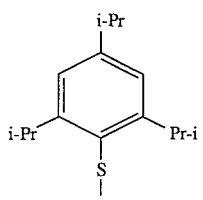
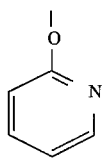
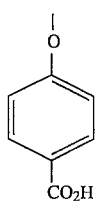
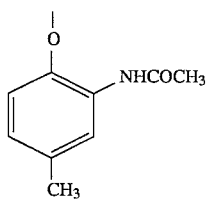
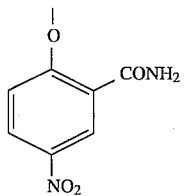
OC$_{12}$H$_{25}$-n
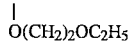
O(CH$_2$)$_2$OC$_2$H$_5$
SO$_2$Ph
O(CH$_2$)$_2$CONH(CH$_2$)$_2$OCH$_3$
-continued
C-264
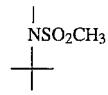
NSO$_2$CH$_3$
C-265
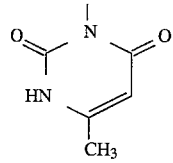
C-266
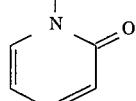
C-267
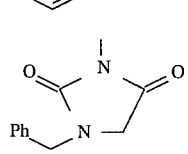
C-268
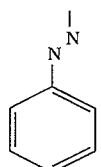
C-269
C-270
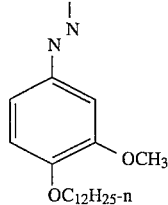
C-271
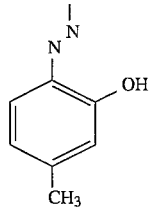
C-272
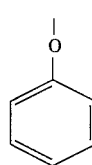
C-273
C-274
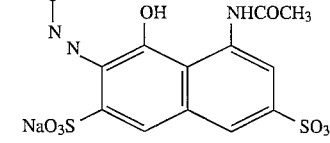
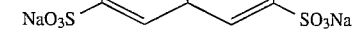
C-275
C-276
C-277
C-278
C-279
C-280
C-281
C-282
C-283

-continued
C-284
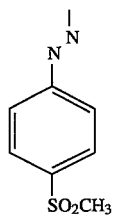
C-284
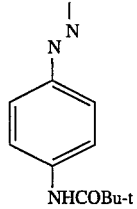
C-285
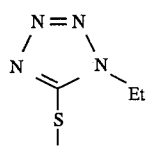
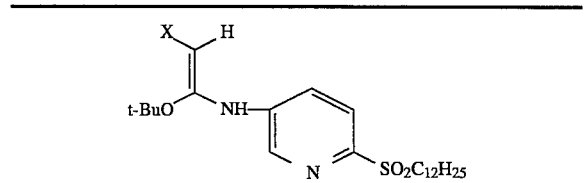
where X is:-
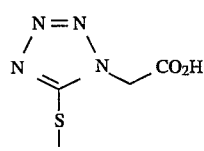
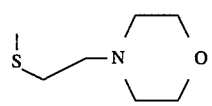
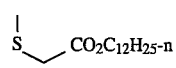
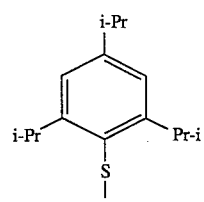
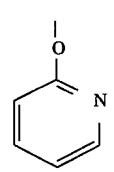
-continued
C-291
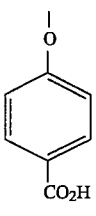
C-292
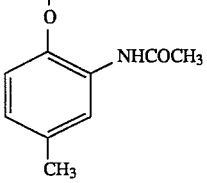
C-293
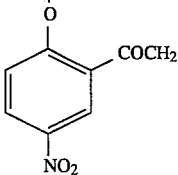
C-294
|
OC₁₂H₂₅-n
C-295
|
O(CH₂)₂OC₂H₅
C-296
|
SO₂Ph
C-297
|
O(CH₂)₂CONH(CH₂)₂OCH₃
C-298
|
NSO₂CH₃
—+—
C-299
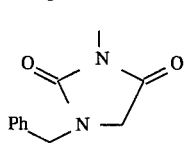
C-300
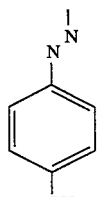
C-301
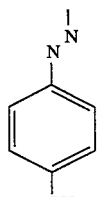
C-302
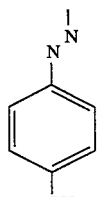

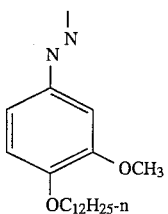
C-303
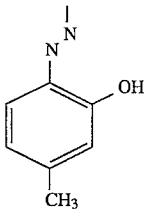
C-304
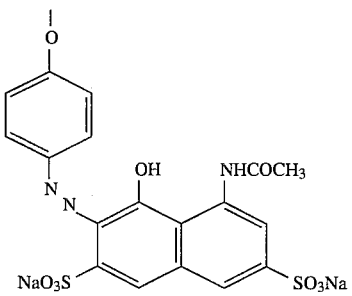
C-305
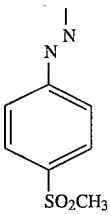
C-306
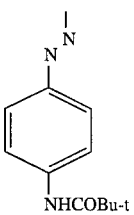
C-307
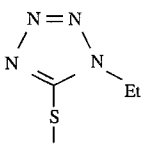
C-308
where X is:-
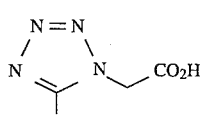
C-309
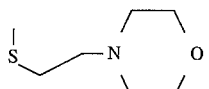
C-310
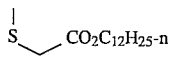
C-311
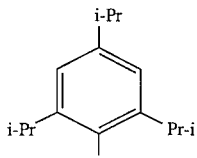
C-312
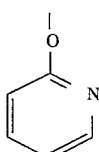
C-313
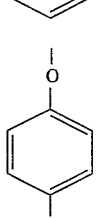
C-314
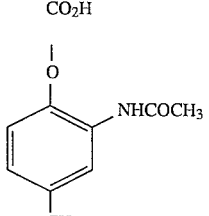
C-315
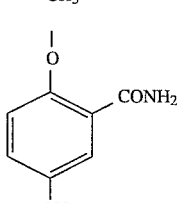
C-316
—OC₁₂H₂₅-n
C-317
—O(CH₂)₂OC₂H₅
C-318
—SO₂Ph
C-319
—O(CH₂)₂CONH(CH₂)₂OCH₃
C-320
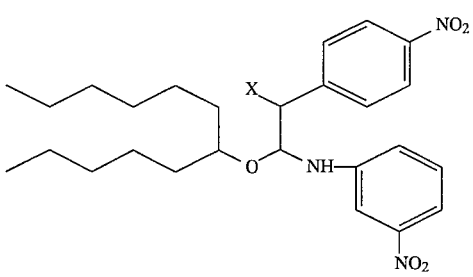

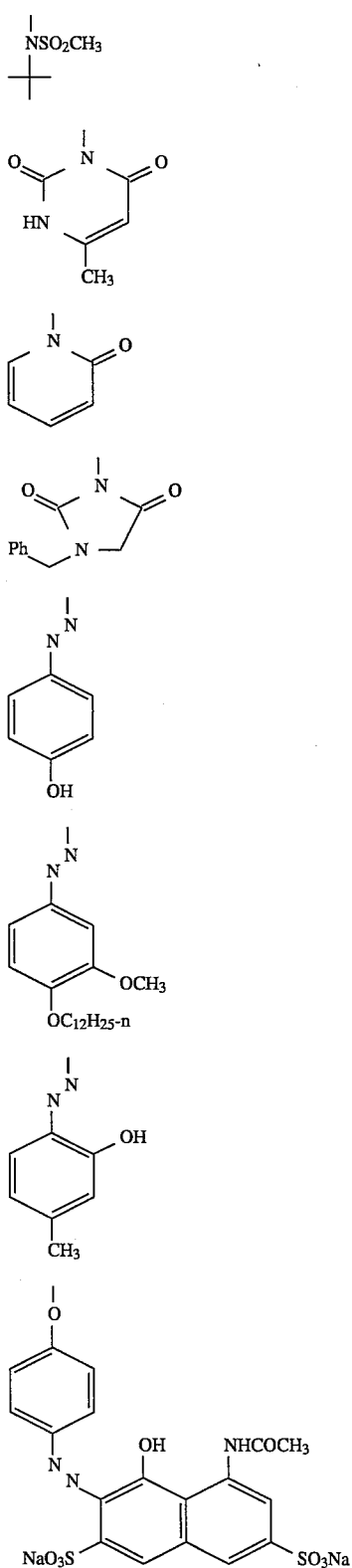
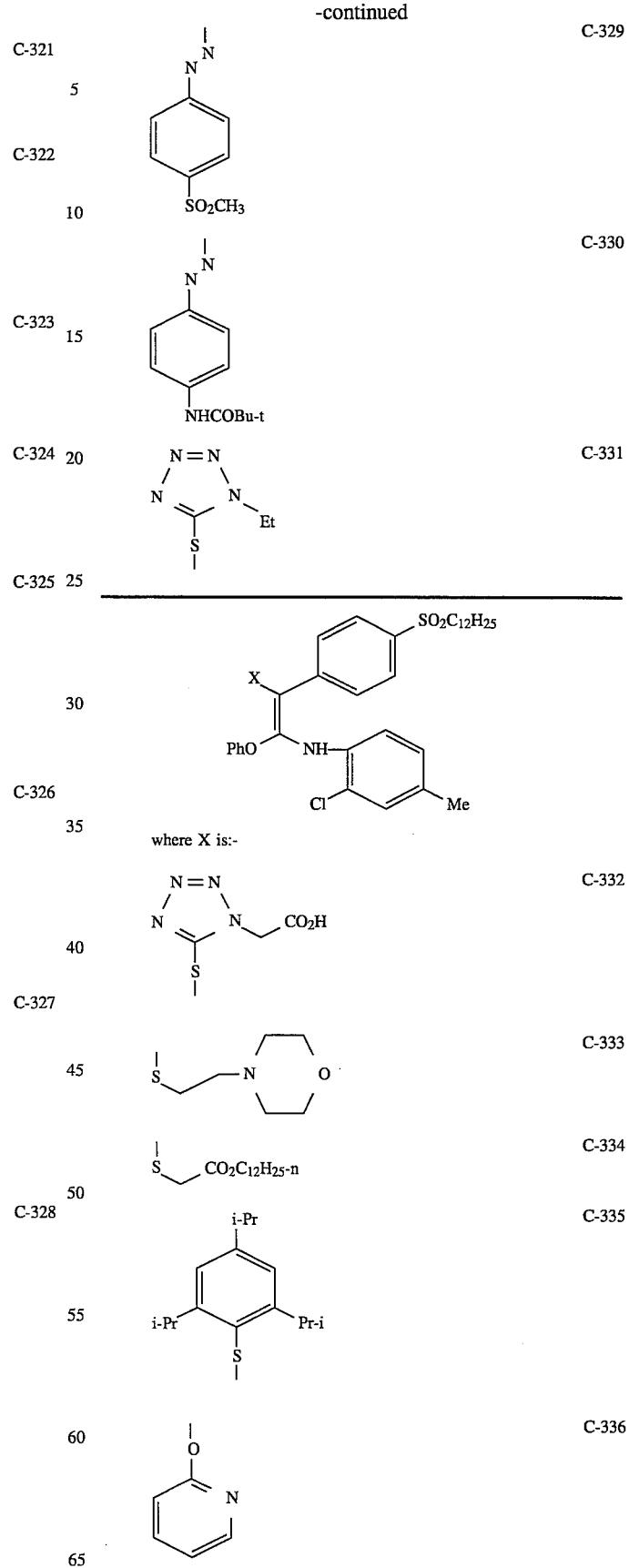

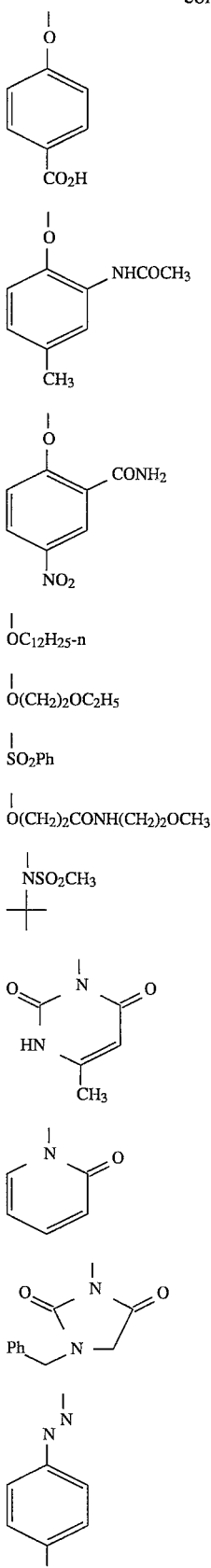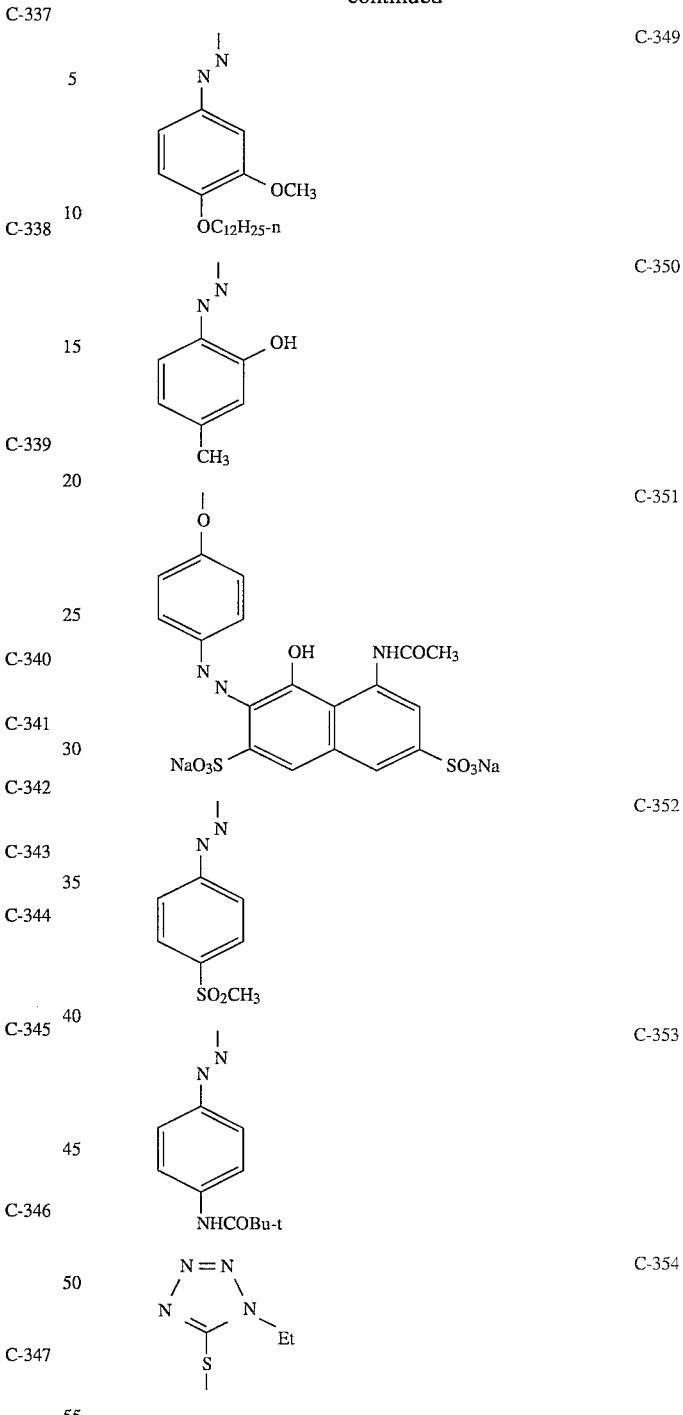

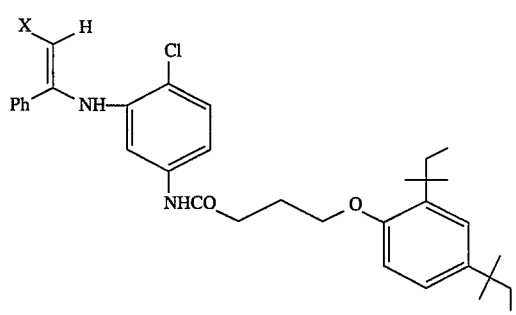
where X is:-
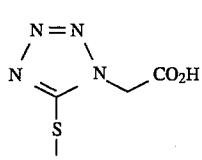 C-355
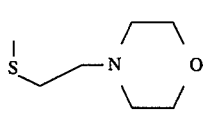 C-356
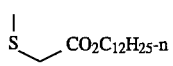 C-357
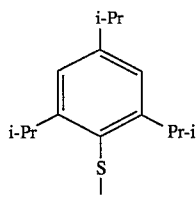 C-358
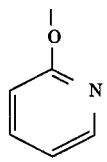 C-359
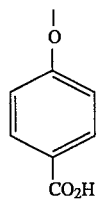 C-360
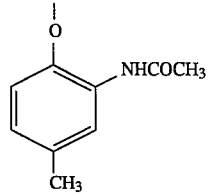 C-361
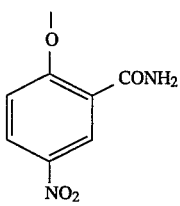 C-362
$OC_{12}H_{25}$-n C-363
$O(CH_2)_2OC_2H_5$ C-364
$SO_2Ph$ C-365
$O(CH_2)_2CONH(CH_2)_2OCH_3$ C-366
 C-367
 C-368
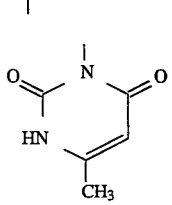 C-369
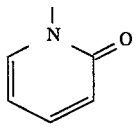 C-370
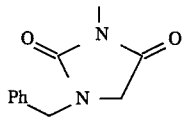 C-371
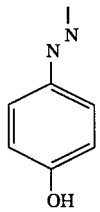 C-372
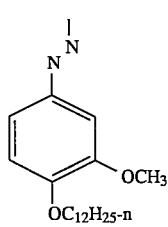 C-373
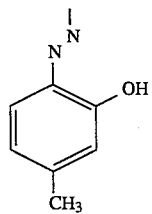

-continued
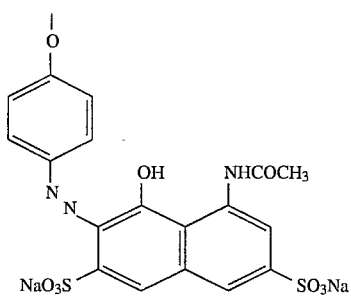
C-374
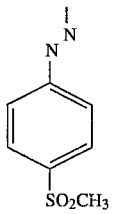
C-375
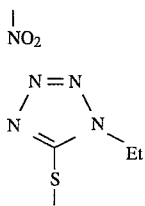
C-376
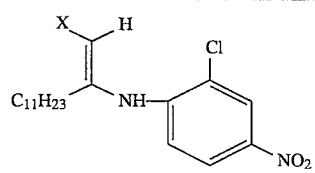
where X is:-
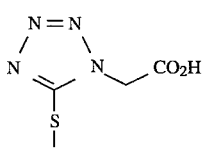
C-377
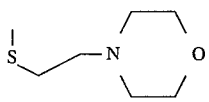
C-378
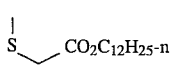
C-379
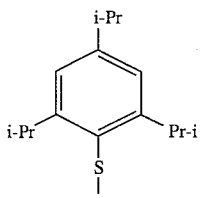
C-380
-continued
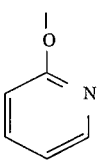
C-382
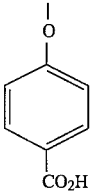
C-383
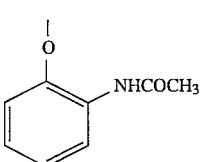
C-384
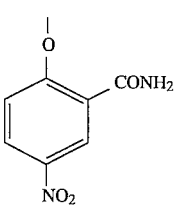
C-385
OC₁₂H₂₅-n
C-386
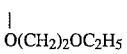
O(CH₂)₂OC₂H₅
C-387
SO₂Ph
C-388
O(CH₂)₂CONH(CH₂)₂OCH₃
C-389
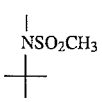
NSO₂CH₃
C-390
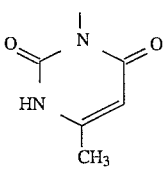
C-391
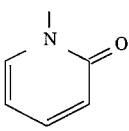
C-392
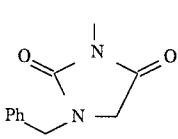
C-393
C-381 where X is:-

| | |
|---|---|
| C-394 (structure: N=N-C6H4-OH) | |
| C-395 (structure: N=N-C6H3(OCH3)(OC12H25-n)) | C-401 (tetrazole-S-CH3, N-CH2CO2H) |
| C-396 (structure: N=N-C6H3(OH)(CH3)) | C-402 (S-CH2CH2-morpholine) |
| C-397 (naphthol azo with OPh, OH, NHCOCH3, 2×SO3Na) | C-403 (S-CH2-CO2C12H25-n) |
| C-398 (N=N-C6H4-SO2CH3) | C-404 (S-C6H2(i-Pr)3) |
| C-399 (NO2) | C-405 (O-pyridin-2-yl) |
| C-400 (tetrazole-S-CH3, N-Et) | C-406 (O-C6H4-CO2H) |
| | C-407 (O-C6H3(NHCOCH3)(CH3)) |
| | C-408 (O-C6H3(COCH2-)(NO2)) |
| | C-409 OC12H25-n |
| | C-410 O(CH2)2OC2H5 |
| | C-411 SO2Ph |
| | C-412 O(CH2)2CONH(CH2)2OCH3 |

(Bottom structure: vinyl compound with X, i-Pr, NH-C6H3(Cl)(NO2), and C6H4-SO2C16H33)

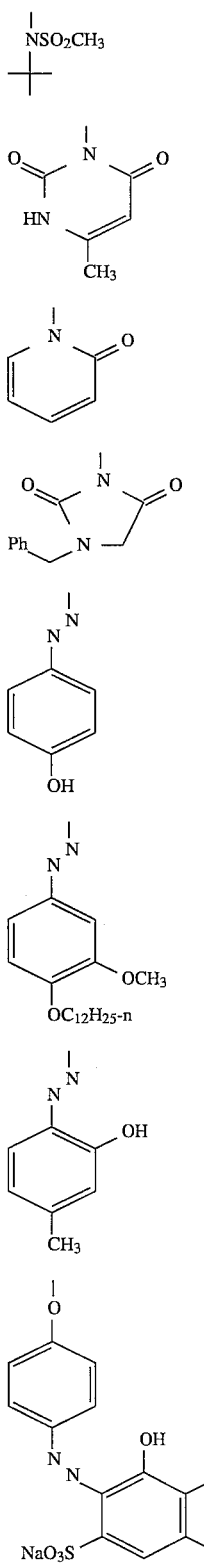
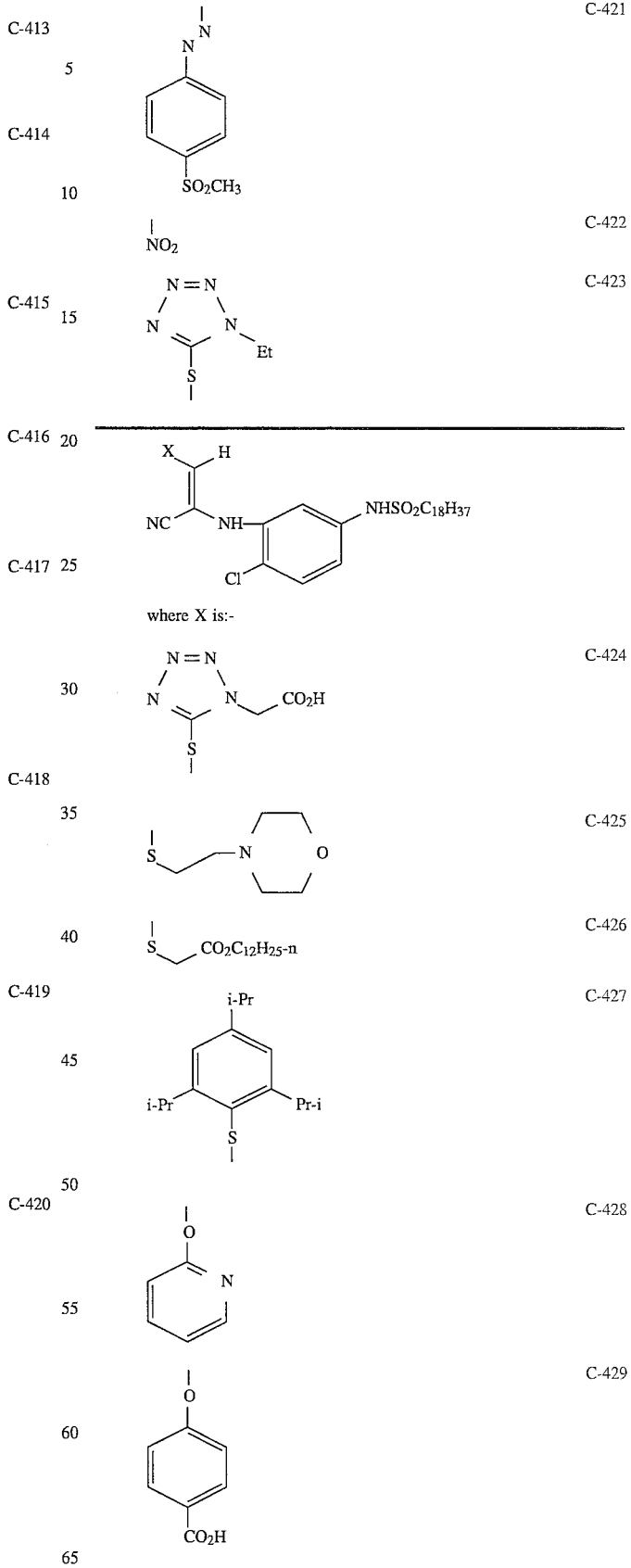

-continued
C-430 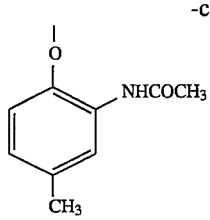
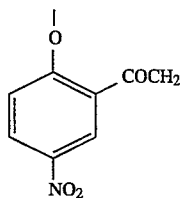
C-431 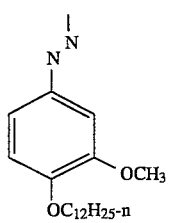
C-432 
C-433 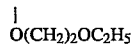
C-434 
C-435 
C-436 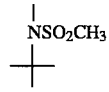
C-437 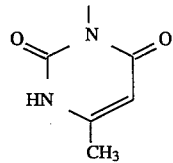
C-438 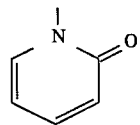
C-439 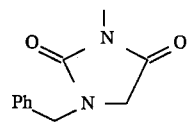
C-440 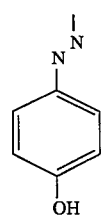
C-441
C-442
C-443
C-444
C-445 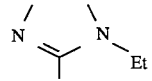
C-446 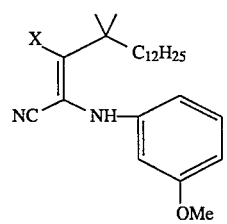
where X is:-

-continued
C-447 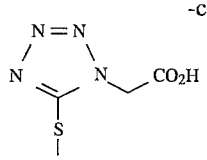
C-448 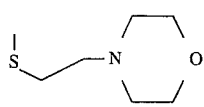
C-449 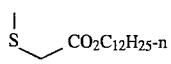
C-450 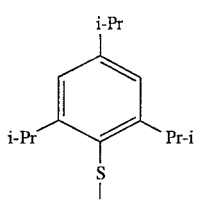
C-451 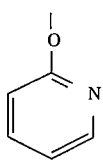
C-452 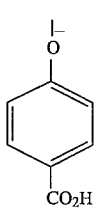
C-453 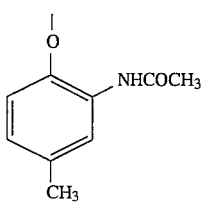
C-454 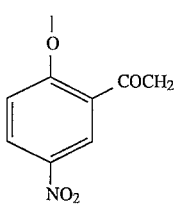
C-455 
OC$_{12}$H$_{25}$-n
C-456 
O(CH$_2$)$_2$OC$_2$H$_5$
C-457 
SO$_2$Ph
C-458 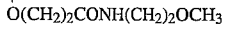
O(CH$_2$)$_2$CONH(CH$_2$)$_2$OCH$_3$
-continued
C-459 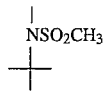
C-460 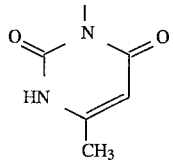
C-461 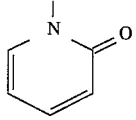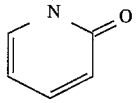
C-462 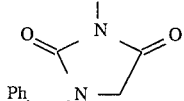
C-463 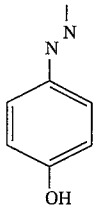
C-464 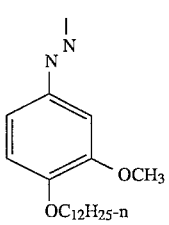
C-465 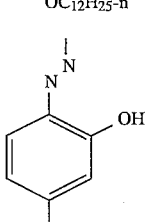
C-466 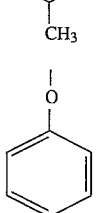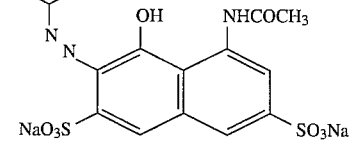

-continued
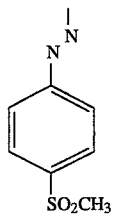 C-467
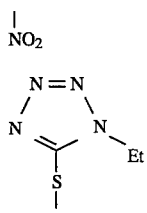 C-468
C-469
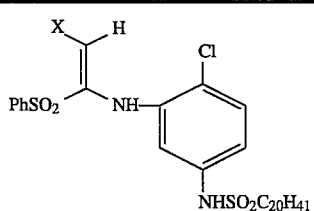
where X is:-
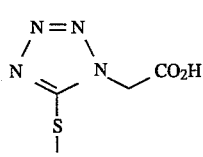 C-470
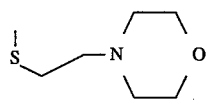 C-471
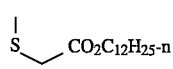 C-472
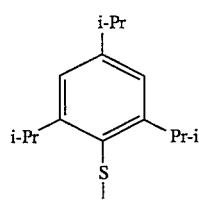 C-473
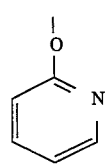 C-474
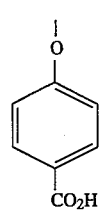 C-475
-continued
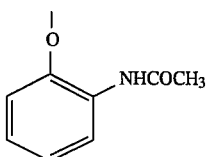 C-476
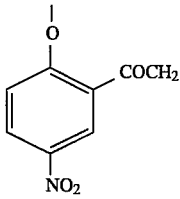 C-477
$OC_{12}H_{25}$-n  C-478
$O(CH_2)_2OC_2H_5$  C-479
$SO_2Ph$  C-480
$O(CH_2)_2CONH(CH_2)_2OCH_3$  C-481
 C-482
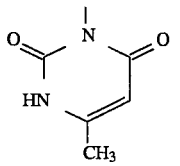 C-483
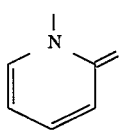 C-484
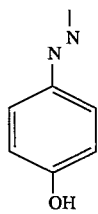 C-485
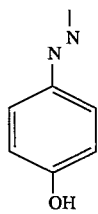 C-486

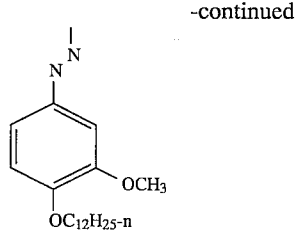 C-487
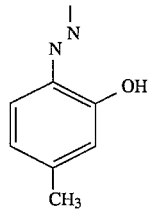 C-488
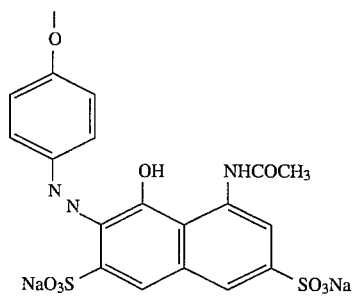 C-489
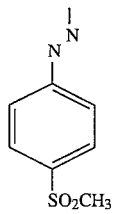 C-490
 C-491
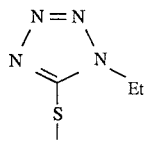 C-492
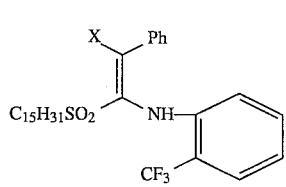
where X is:-
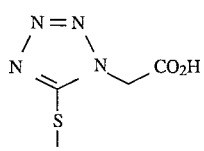 C-493
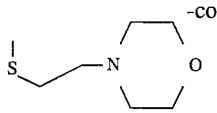 C-494
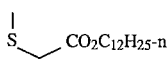 C-495
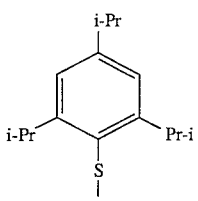 C-496
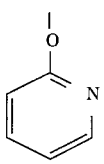 C-497
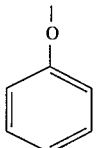 C-498
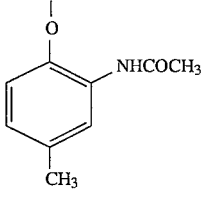 C-499
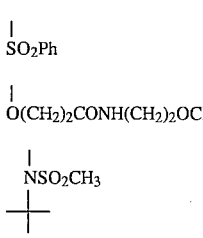 C-500
 OC$_{12}$H$_{25}$-n   C-501
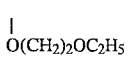 O(CH$_2$)$_2$OC$_2$H$_5$   C-502
 SO$_2$Ph   C-503
 O(CH$_2$)$_2$CONH(CH$_2$)$_2$OCH$_3$   C-504
 NSO$_2$CH$_3$   C-505

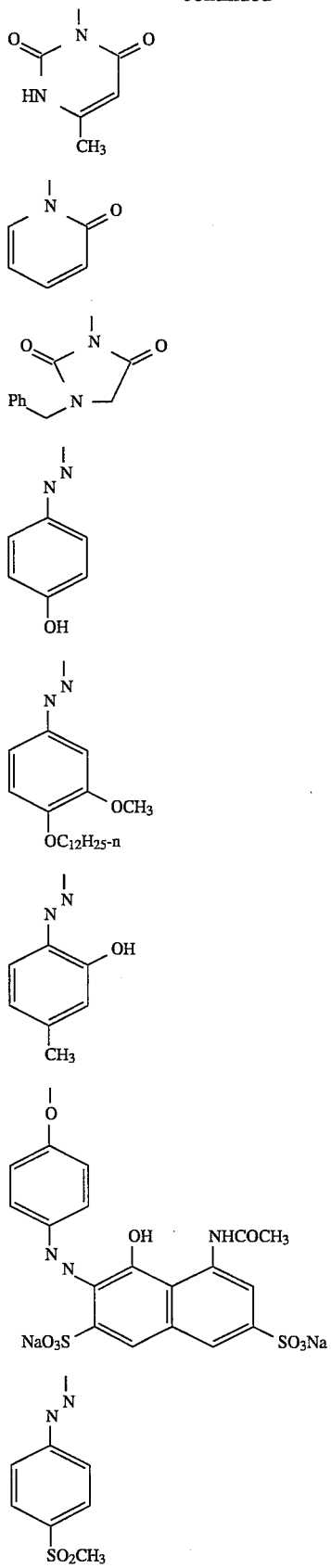

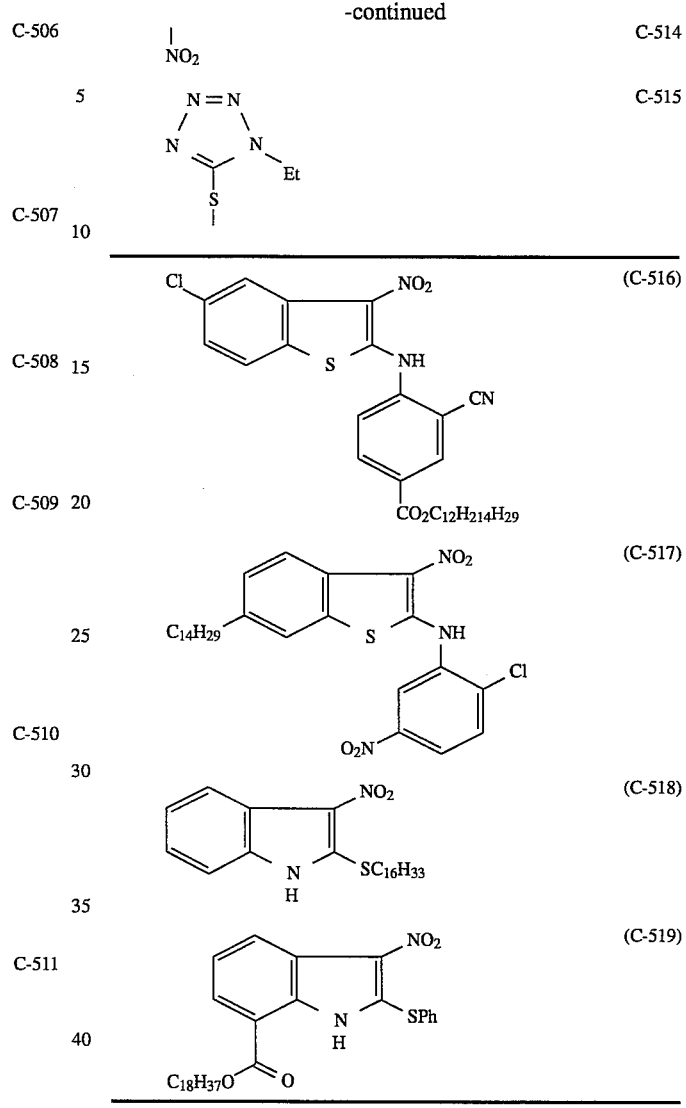

The materials of the invention can be used in any of the ways and in any of the combinations known in the art. Typically, the invention materials are incorporated in a silver halide emulsion and the emulsion coated as a layer on a support to form part of a photographic element. Alternatively, they can be incorporated at a location adjacent to the silver halide emulsion layer where, during development, they will be in reactive association with development products such as oxidized color developing agent. Thus, as used herein, the term "associated" signifies that the compound is in the silver halide emulsion layer or in an adjacent location where, during processing, it is capable of reacting with silver halide development products.

To control the migration of various components, it may be desirable to include a high molecular weight hydrophobe or "ballast" group in the component molecule. Representative ballast groups include substituted or unsubstituted alkyl or aryl groups containing 8 to 42 carbon atoms. Representative substituents on such groups include alkyl, aryl, alkoxy, aryloxy, alkylthio, hydroxy, halogen, alkoxycarbonyl, aryloxcarbonyl, carboxy, acyl, acyloxy, amino, anilino, carbonamido, carbamoyl, alkylsulfonyl, arysulfonyl, sulfonamido, and sulfamoyl groups wherein the substituents typically contain 1 to 42 carbon atoms. Such substituents can also be further substituted.

The photographic elements can be single color elements or multicolor elements. Multicolor elements contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

If desired, the photographic element can be used in conjunction with an applied magnetic layer as described in *Research Disclosure*, November 1992, Item 34390 published by Kenneth Mason Publications, Ltd., Dudley Annex, 12a North Street, Emsworth, Hampshire P010 7DQ, ENGLAND.

In the following discussion of suitable materials for use in the emulsions and elements of this invention, reference will be made to *Research Disclosure*, December 1989, Item 308119, available as described above, which will be identified hereafter by the term "Research Disclosure." The contents of the Research Disclosure, including the patents and publications referenced therein, are incorporated herein by reference, and the Sections hereafter referred to are Sections of the Research Disclosure.

The silver halide emulsions employed in the elements of this invention can be either negative-working or positive-working. Suitable emulsions and their preparation as well as methods of chemical and spectral sensitization are described in Sections I through IV. Color materials and development modifiers are described in Sections VII and XXI. Vehicles are described in Section IX, and various additives such as brighteners, antifoggants, stabilizers, light absorbing and scattering materials, hardeners, coating aids, plasticizers, lubricants and matting agents are described, for example, in Sections V, VI, VIII, X, XI, XII, and XVI. Manufacturing methods are described in Sections XIV and XV, other layers and supports in Sections XIII and XVII, processing methods and agents in Sections XIX and XX, and exposure alternatives in Section XVIII.

Coupling-off groups are well known in the art. Such groups can determine the chemical equivalency of a coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, dye hue adjustment, development acceleration or inhibition, bleach acceleration or inhibition, electron transfer facilitation, color correction and the like.

The presence of hydrogen at the coupling site provides a 4-equivalent coupler, and the presence of another coupling-off group usually provides a 2-equivalent coupler. Representative classes of such coupling-off groups include, for example, chloro, alkoxy, aryloxy, hetero-oxy, sulfonyloxy, acyloxy, acyl, heterocyclyl, sulfonamido, mercaptotetrazole, benzothiazole, mercaptopropionic acid, phosphonyloxy, arylthio, and arylazo. These coupling-off groups are described in the art, for example, in U.S. Pat. Nos. 2,455, 169, 3,227,551, 3,432,521, 3,476,563, 3,617,291, 3,880,661, 4,052,212 and 4,134,766; and in U.K. Patents and published application Nos. 1,466,728, 1,531,927, 1,533,039, 2,006, 755A and 2,017,704A, the disclosures of which are incorporated herein by reference.

Image dye-forming couplers may be included in the element such as couplers that form cyan dyes upon reaction with oxidized color developing agents which are described in such representative patents and publications as: U.S. Pat. Nos. 2,367,531, 2,423,730, 2,474,293, 2,772,162, 2,895, 826, 3,002,836, 3,034,892, 3,041,236, 4,333,999, 4,883,746 and "Farbkuppler-eine LiteratureUbersicht," published in Agfa Mitteilungen, Band III, pp. 156–175 (1961). Preferably such couplers are phenols and naphthols that form cyan dyes on reaction with oxidized color developing agent.

Couplers that form magenta dyes upon reaction with oxidized color developing agent are described in such representative patents and publications as: U.S. Pat. Nos. 2,311, 082, 2,343,703, 2,369,489, 2,600,788, 2,908,573, 3,062,653, 3,152,896, 3,519,429, and "Farbkuppler-eine LiteratureUbersicht," published in Agfa Mitteilungen, Band III, pp. 126–156 (1961). Preferably such couplers are pyrazolones, pyrazolotriazoles, or pyrazolobenzimidazoles that form magenta dyes upon reaction with oxidized color developing agents.

Couplers that form yellow dyes upon reaction with oxidized and color developing agent are described in such representative patents and publications as: U.S. Pat. Nos. 2,298,443, 2,407,210, 2,875,057, 3,048,194, 3,265,506, 3,447,928, 4,022,620, 4,443,536, and "Farbkuppler-eine LiteratureUbersicht," published in Agfa Mitteilungen, Band III, pp. 112–126 (1961). Such couplers are typically open chain ketomethylene compounds.

Couplers that form colorless products upon reaction with oxidized color developing agent are described in such representative patents as: U.K. Patent No. 861,138; U.S. Pat. Nos. 3,632,345, 3,928,041, 3,958,993 and 3,961,959. Typically such couplers are cyclic carbonyl containing compounds that form colorless products on reaction with an oxidized color developing agent.

Couplers that form black dyes upon reaction with oxidized color developing agent are described in such representative patents as U.S. Patent Nos. 1,939,231; 2,181,944; 2,333,106; and 4,126,461; German OLS No. 2,644,194 and German OLS No. 2,650,764. Typically, such couplers are resorcinols or m-aminophenols that form black or neutral products on reaction with oxidized color developing agent.

In addition to the foregoing, so-called "universal" or "washout" couplers may be employed. These couplers do not contribute to image dye-formation. Thus, for example, a naphthol having an unsubstituted carbamoyl or one substituted with a low molecular weight substituent at the 2- or 3- position may be employed. Couplers of this type are described, for example, in U.S. Pat. Nos. 5,026,628, 5,151, 343, and 5,234,800.

It may be useful to use a combination of Couplers any of which may contain known ballasts or coupling-off groups such as those described in U.S. Pat. Nos. 4,301,235; 4,853, 319 and 4,351,897. The coupler may contain solubilizing groups such as described in U.S. Pat. No. 4,482,629. The coupler may also be used in association with "wrong" colored couplers (e.g. to adjust levels of interlayer correction) and, in color negative applications, with masking couplers such as those described in EP 213,490; Japanese Published Application 58-172,647; U.S. Pat. Nos. 2,983, 608; 4,070,191; and 4,273,861; German Applications DE 2,706,117 and DE 2,643,965; U.K. Patent 1,530,272; and Japanese Application A-113935. The masking couplers may be shifted or blocked, if desired.

For example, in a color negative element, the materials of the invention may replace or supplement the materials of an element comprising a support bearing the following layers from top to bottom:
(1) one or more overcoat layers containing ultraviolet absorber(s);
(2) a two-coat yellow pack with a fast yellow layer containing "Coupler 1": Benzoic acid, 4-chloro-3-((2-(4-ethoxy-2,5-dioxo-3-(phenylmethyl)-1-imidazolidinyl)-3-(4-methoxyphenyl)-1,3 -dioxopropyl)amino)-, dodecyl ester and a slow yellow layer containing the same compound together with "Coupler 2": Propanoic acid, 2-[[5-[[4-[2-[[[2,4 -bis(1,1-dimethylpropyl)phenoxy]acetyl ]amino]-5-[(2,2,3,3,4,4,4-heptafluoro-1-oxobutyl)amino]-4 -hydroxyphenoxy]-2,3-dihydroxy-6-[(propylamino)carbonyl]phenyl]thio]-1,3,4-thiadiazol-2-yl]thio]-, methyl ester and "Coupler 3": 1-((dodecyloxy)carbonyl)ethyl(3-chloro-4-((3-(2-chloro-4-((1 -tridecanoylethoxy)carbonyl)anilino)-3-oxo-2 -((4)(5)(6)-(phenoxycarbonyl)-1H-benzotriazol-1 -yl)propanoyl)amino))benzoate;
(3) an interlayer containing fine metallic silver;
(4) a triple-coat magenta pack with a fast magenta layer containing "Coupler 4": Benzamide, 3-((2-(2,4 -bis(1,1-dimethylpropyl)phenoxy)-1-oxobutyl)amino)-N-(4,5-dihydro-5-oxo-1-(2,4,6-trichlorophenyl)-1H-pyrazol-3-yl)-, "Coupler 5": Benzamide, 3-((2-(2,4 -bis(1,1-dimethylpropyl)phenoxy)-1-oxobutyl)amino)-N-(4',5'-dihydro-5'-oxo-1'-(2,4,6-trichlorophenyl) (1,4'-bi-1H-pyrazol)-3'-yl)-, "Coupler 6": Carbamic acid, (6-(((3-(dodecyloxy)propyl)amino)carbonyl)-5 -hydroxy-1-naphthalenyl)-, 2-methylpropyl ester, "Coupler 7": Acetic acid, ((2-((3-(((3 -(dodecyloxy)propyl)amino)carbonyl)-4-hydroxy-8-(((2 -methylpropoxy)carbonyl)amino)-1-naphthalenyl)oxy)ethyl)thio)-, and "Coupler 8" Benzamide, 3-((2-(2,4 -bis(1,1-dimethylpropyl)phenoxy)-1-oxobutyl)amino)-N-(4,5-dihydro-4-((4-methoxyphenyl)azo)-5-oxo-1-(2,4,6 -trichlorophenyl)-1H-pyrazol-3-yl)-; a mid-magenta layer and a slow magenta layer each containing "Coupler 9": a ternary copolymer containing by weight in the ratio 1:1:2 2-Propenoic acid butyl ester, styrene, and N-[1-(2,4,6-trichlorophenyl)-4,5-dihydro-5-oxo-1H-pyrazol-3-yl]-2-methyl-2-propenamide; and "Coupler 10": Tetradecanamide, N-(4-chloro-3-((4-((4 -((2,2-dimethyl-1-oxopropyl)amino)phenyl)azo)-4,5 -dihydro-5-oxo-1-(2,4,6-trichlorophenyl)-1H-pyrazol-3 -yl)amino)phenyl)-, in addition to Couplers 3 and 8;
(5) an interlayer;
(6) a triple-coat cyan pack with a fast cyan layer containing Couplers 6 and 7; a mid-cyan containing Coupler 6 and "Coupler 11": 2,7-Naphthalenedisulfonic acid, 5-(acetylamino)-3-((4-(2-((3-(((3-(2,4-bis(1,1 -dimethylpropyl)phenoxy)propyl)amino)carbonyl)-4 -hydroxy-1-naphthalenyl)oxy)ethoxy)phenyl)azo)-4 -hydroxy-, disodium salt; and a slow cyan layer containing Couplers 2 and 6;
(7) an undercoat layer containing Coupler 8; and
(8) an antihalation layer.

In a color paper format, the materials of the invention may replace or supplement the materials of an element comprising a support bearing the following layers from top to bottom:
(1) one or more overcoats;
(2) a cyan layer containing "Coupler 1": Butanamide, 2-(2, 4-bis(1,1-dimethylpropyl)phenoxy)-N-(3,5 -dichloro-2-hydroxy-4-methylphenyl)-, "Coupler 2": Acetamide, 2-(2,4-bis(1,1-dimethylpropyl)phenoxy)-N-(3,5-dichloro-2-hydroxy-4-, and UV Stabilizers: Phenol, 2-(5-chloro-2H-benzotriazol-2-yl)-4,6-bis(1,1 -dimethylethyl)-; Phenol, 2-(2H-benzotriazol-2-yl)-4 -(1,1-dimethylethyl)-; Phenol, 2-(2H-benzotriazol-2-yl)-4-(1,1-dimethylethyl)-6-(1-methylpropyl)-; and Phenol, 2-(2H-benzotriazol-2-yl)-4,6-bis(1,1-dimethylpropyl)- and a poly(t-butylacrylamide) dye stabilizer;
(3) an interlayer;
(4) a magenta layer containing "Coupler 3": Octanamide, 2-[2,4-bis(1,1-dimethylpropyl)phenoxy]-N-[2-(7-chloro-6-methyl-1H-pyrazolo[1,5 -b][1,2,4]triazol-2-yl)propyl]- together with 1,1' -Spirobi(1H-indene), 2,2',3,3'-tetrahydro-3,3,3',3' -tetramethyl-5,5', 6,6'-tetrapropoxy-;
(5) an interlayer; and
(6) a yellow layer containing "Coupler 4": 1-Imidazolidineacetamide, N-(5-((2-(2,4-bis(1,1 -dimethylpropyl)phenoxy)-1-oxobutyl)amino)-2 -chlorophenyl)-.alpha.-(2,2-dimethyl-1-oxopropyl)-4 -ethoxy-2,5-dioxo-3-(phenylmethyl)-.

In a reversal format, the materials of the invention may replace or supplement the materials of an element comprising a support bearing the following layers from top to bottom:
(1) one or more overcoat layers;
(2) a nonsensitized silver halide containing layer;
(3) a triple-coat yellow layer pack with a fast yellow layer containing "Coupler 1": Benzoic acid, 4 -(1-(((2-chloro-5-((dodecylsulfonyl)amino)phenyl)amino)carbonyl)- 3,3-dimethyl-2-oxobutoxy)-, 1-methylethyl ester; a mid yellow layer containing Coupler 1 and "Coupler 2": Benzoic acid, 4-chloro-3-[[2-[4-ethoxy-2,5-dioxo-3-(phenylmethyl)-1 -imidazolidinyl]-4,4-dimethyl-1,3-dioxopentyl] amino]-, dodecylester; and a slow yellow layer also containing Coupler 2;
(4) an interlayer;
(5) a layer of fine-grained silver;
(6) an interlayer;
(7) a triple-coated magenta pack with a fast magenta layer containing "Coupler 3": 2-Propenoic acid, butyl ester, polymer with N-[1-(2,5-dichlorophenyl)-4,5 -dihydro-5-oxo-1H-pyrazol-3-yl]-2-methyl-2-propenamide; "Coupler 4": Benzamide, 3-((2-(2,4-bis(1,1 -dimethylpropyl)phenoxy)-1-oxobutyl)amino)-N-(4,5 -dihydro-5-oxo-1-(2,4,6-trichlorophenyl)-1H-pyrazol-3 -yl)-; and "Coupler 5": Benzamide, 3-(((2,4-bis(1,1 -dimethylpropyl)phenoxy)acetyl)amino)-N-(4,5-dihydro-5 -oxo-1-(2,4,6-trichlorophenyl)-1H-pyrazol-3-yl)-; and containing the stabilizer 1,1'-Spirobi(1H-indene), 2,2',3,3'-tetrahydro-3, 3,3',3'-tetramethyl-5,5',6,6' -tetrapropoxy-; and in the slow magenta layer Couplers 4 and 5 with the same stabilizer;
(8) one or more interlayers possibly including fine-grained nonsensitized silver halide;
(9) a triple-coated cyan pack with a fast cyan layer containing "Coupler 6": Tetradecanamide, 2-(2 -cyanophenoxy)-N-(4-((2,2,3,3,4,4,4-heptafluoro-1 -oxobutyl)amino)-3- hydroxyphenyl)-; a mid cyan containing "Coupler 7": Butanamide, N-(4-((2-(2,4-bis(1,1-dimethylpropyl)phenoxy)-1-oxobutyl)amino)-2-hydroxyphenyl)-2,2,3,3,4,4,4-heptafluoro- and "Coupler 8": Hexanamide, 2-(2,4-bis(1,1-dimethylpropyl)phenoxy)-N-(4-((2,2,3,3,4,4,4-heptafluoro-1-oxobutyl)amino)-3-hydroxyphenyl)-;

(10) one or more interlayers possibly including fine-grained nonsensitized silver halide; and

(11) an antihalation layer.

The invention materials may be used in association with materials that accelerate or otherwise modify the processing steps e.g. of bleaching or fixing to improve the quality of the image. Bleach accelerator releasing couplers such as those described in EP 193,389; EP 301,477; U.S. Pat. Nos. 4,163,669; 4,865,956; and 4,923,784, may be useful. Also contemplated is use of the compositions in association with nucleating agents, development accelerators or their precursors (UK Patent 2,097,140; U.K. Patent 2,131,188); electron transfer agents (U.S. Pat. Nos. 4,859,578; 4,912,025); antifogging and anti color-mixing agents such as derivatives of hydroquinones, aminophenols, amines, gallic acid; catechol; ascorbic acid; hydrazides; sulfonamidophenols; and non color-forming couplers.

The invention materials may also be used in combination with filter dye layers comprising colloidal silver sol or yellow, cyan, and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. Nos. 4,420,556; and 4,543,323.) Also, the compositions may be blocked or coated in protected form as described, for example, in Japanese Application 61/258,249 or U.S. 5,019,492.

The invention materials may further be used in combination with image-modifying compounds such as "Developer Inhibitor-Releasing" compounds (DIR's). DIR's useful in conjunction with the compositions of the invention are known in the art and examples are described in U.S. Pat. Nos. 3,137,578; 3,148,022; 3,148,062; 3,227,554; 3,384,657; 3,379,529; 3,615,506; 3,617,291; 3,620,746; 3,701,783; 3,733,201; 4,049,455; 4,095,984; 4,126,459; 4,149,886; 4,150,228; 4,211,562; 4,248,962; 4,259,437; 4,362,878; 4,409,323; 4,477,563; 4,782,012; 4,962,018; 4,500,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346,899; 362,870; 365,252; 365,346; 373,382; 376,212; 377,463; 378,236; 384,670; 396,486; 401,612; 401,613.

Such compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference. Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazotes, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazoles. In a preferred embodiment, the inhibitor moiety or group is selected from the following formulas:

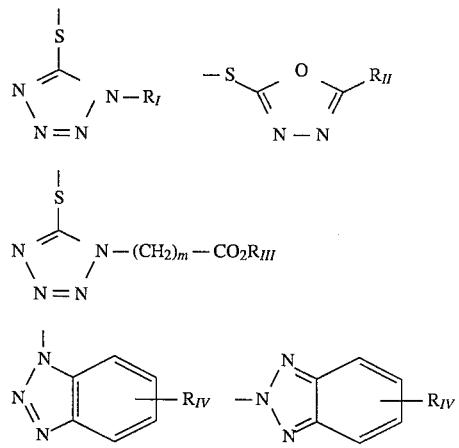

wherein $R_I$ is selected from the group consisting of straight and branched alkyls of from 1 to about 8 carbon atoms, benzyl, phenyl, and alkoxy groups and such groups containing none, one or more than one such substituent; $R_{II}$ is selected from $R_I$ and —$SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, —$COOR_V$ and —$NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

As mentioned, the developer inhibitor-releasing coupler may include a timing group, which produces the time-delayed release of the inhibitor group such as groups utilizing the cleavage reaction of a hemiacetal (U.S. Pat. No. 4,146,396, Japanese Applications 60-249148; 60-249149); groups using an intramolecular nucleophilic substitution reaction (U.S. Pat. No. 4,248,962); groups utilizing an electron transfer reaction along a conjugated system (U.S. Pat. Nos. 4,409,323; 4,421,845; Japanese Applications 57-188035; 58-98728; 58-209736; 58-209738) groups utilizing ester hydrolysis (German Patent Application (OLS) No. 2,626,315); groups utilizing the cleavage of imino ketals (U.S. Pat. No. 4,546,073); groups that function as a coupler or reducing agent after the coupler reaction (U.S. Pat. Nos. 4,438,193; 4,618,571) and groups that combine the features describe above. It is typical that the timing group or moiety is of one of the formulas:

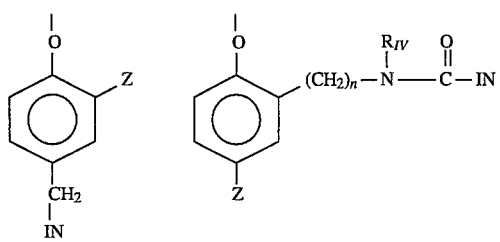

wherein IN is the inhibitor moiety, Z is selected from the group consisting of nitro, cyano, alkylsulfonyl; sulfamoyl (—$SO_2NR_2$); and sulfonamido (—$NRSO_2R$) groups; n is 0 or 1; and $R_{VI}$ is selected from the group consisting of substituted and unsubstituted alkyl and phenyl groups. The oxygen atom of each timing group is bonded to the coupling-off position of the respective coupler moiety of the DIAR.

Suitable developer inhibitor-releasing couplers for use in the present invention include, but are not limited to, the following:

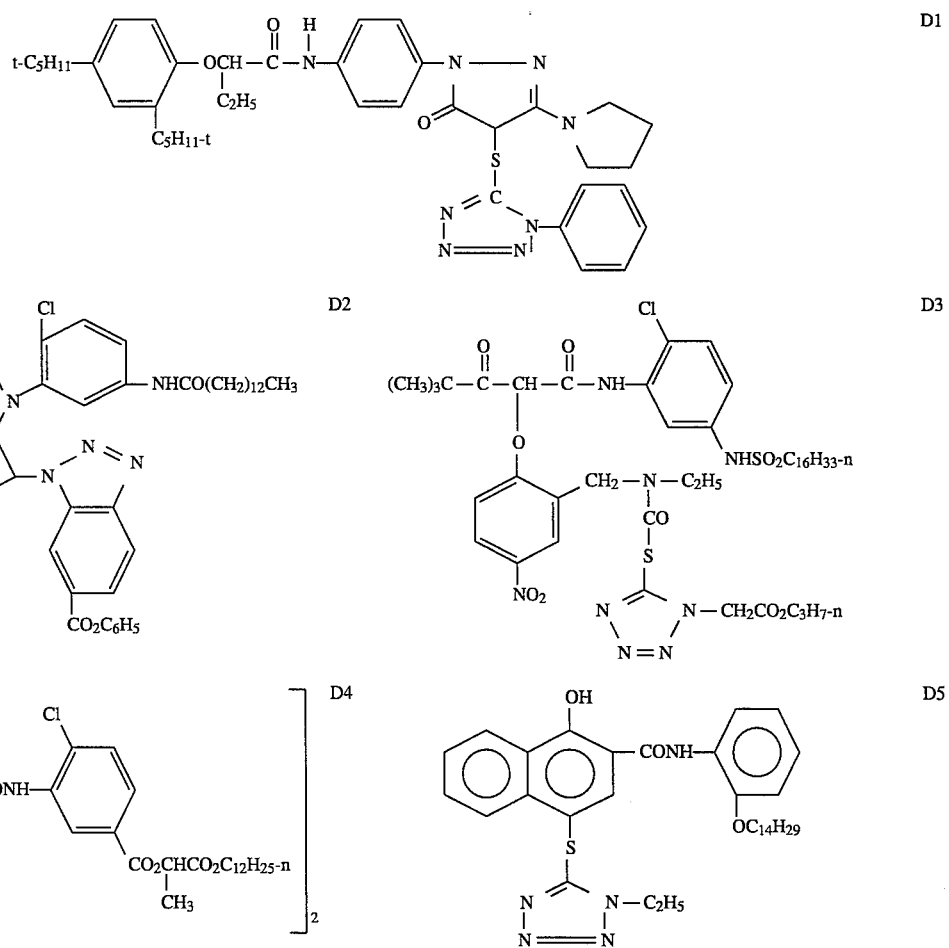

-continued

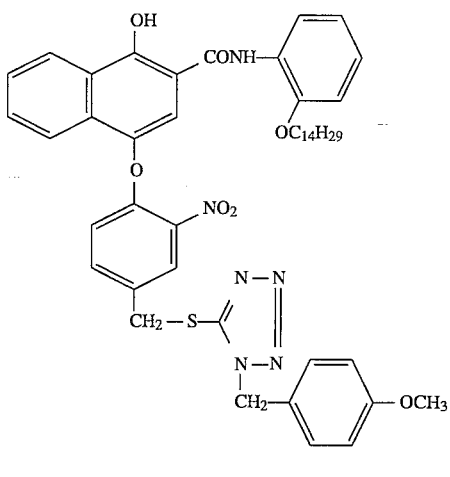 D6

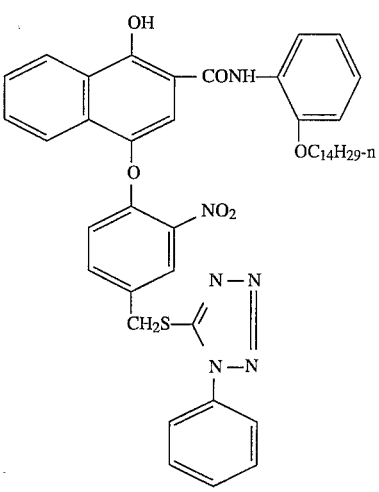 D7

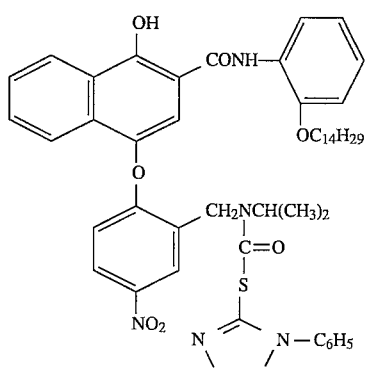 D8

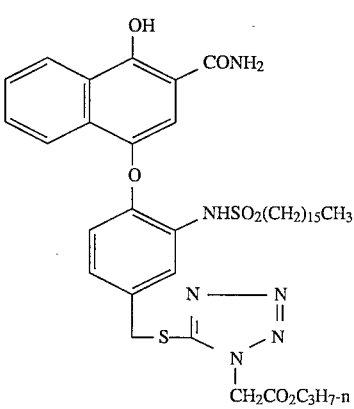 D9

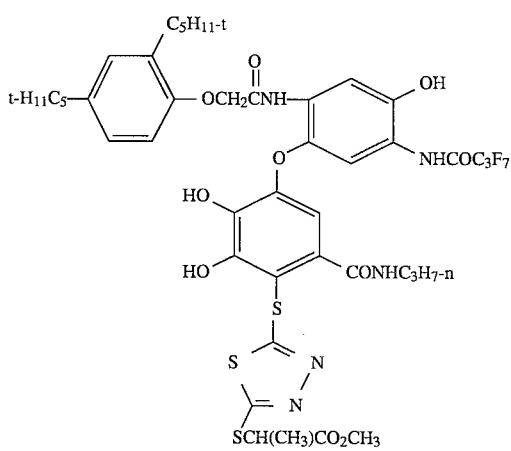 D10

It is also contemplated that the concepts of the present invention may be employed to obtain reflection color prints as described in *Research Disclosure*, November 1979, Item 18716, available from Kenneth Mason Publications, Ltd, Dudley Annex, 12a North Street, Emsworth, Hampshire P0101 7DQ, England, incorporated herein by reference. Materials of the invention may be coated on pH adjusted support as described in U.S. Pat. No. 4,917,994; on a support with reduced oxygen permeability (EP 553,339); with epoxy solvents (EP 164,961); with nickel complex stabilizers (U.S. Pat. Nos. 4,346,165; 4,540,653 and 4,906,559 for example); with ballasted chelating agents such as those in U.S. Pat. No. 4,994,359 to reduce sensitivity to polyvalent cations such as calcium; and with stain reducing compounds such as described in U.S. Pat. No. 5,068,171. Other compounds useful in combination with the invention are disclosed in Japanese Published Applications described in Derwent Abstracts having accession numbers as follows: 90-072,629, 90-072,630; 90-072,631; 90-072,632; 90-072,633; 90-072, 634; 90-077,822; 90-078,229; 90-078,230; 90-079,336; 90-079,337; 90-079,338; 90-079,690; 90-079,691; 90-080, 487; 90-080,488; 90-080,489; 90-080,490; 90-080,491; 90-080,492; 90-080,494; 90-085,928; 90-086,669; 90-086, 670; 90-087,360; 90-087,361; 90-087,362; 90-087,363; 90-087,364; 90-088,097; 90-093,662; 90-093,663; 90-093, 664; 90-093,665; 90-093,666; 90-093,668; 90-094,055; 90-094,056; 90-103,409; 83-62,586; 83-09,959.

Especially useful in this invention are tabular grain silver halide emulsions. Specifically contemplated tabular grain emulsions are those in which greater than 50 percent of the total projected area of the emulsion grains are accounted for by tabular grains having a thickness of less than 0.3 micron (0.5 micron for blue sensitive emulsion) and an average tabularity (T) of greater than 25 (preferably greater than 100), where the term "tabularity" is employed in its art recognized usage as $$T=ECD/t^2$$

where

ECD is the average equivalent circular diameter of the tabular grains in micrometers and t is the average thickness in micrometers of the tabular grains.

The average useful ECD of photographic emulsions can range up to about 10 micrometers, although in practice emulsion ECD's seldom exceed about 4 micrometers. Since both photographic speed and granularity increase with increasing ECD's, it is generally preferred to employ the smallest tabular grain ECD's compatible with achieving aim speed requirements.

Emulsion tabularity increases markedly with reductions in tabular grain thickness. It is generally preferred that aim tabular grain projected areas be satisfied by thin (t<0.2 micrometer) tabular grains. To achieve the lowest levels of granularity it is preferred that aim tabular grain projected areas be satisfied with ultrathin (t<0.06 micrometer) tabular grains. Tabular grain thicknesses typically range down to about 0.02 micrometer. However, still lower tabular grain thicknesses are contemplated. For example, Daubendiek et al U.S. Pat. No. 4,672,027 reports a 3 mole percent iodide tabular grain silver bromoiodide emulsion having a grain thickness of 0.017 micrometer. Ultrathin tabular grain high chloride emulsions are disclosed by Maskasky U.S. Pat. No. 5,217,858.

As noted above tabular grains of less than the specified thickness account for at least 50 percent of the total grain projected area of the emulsion. To maximize the advantages of high tabularity it is generally preferred that tabular grains satisfying the stated thickness criterion account for the highest conveniently attainable percentage of the total grain projected area of the emulsion. For example, in preferred emulsions, tabular grains satisfying the stated thickness criteria above account for at least 70 percent of the total grain projected area. In the highest performance tabular grain emulsions, tabular grains satisfying the thickness criteria above account for at least 90 percent of total grain projected area.

Suitable tabular grain emulsions can be selected from among a variety of conventional teachings, such as those of the following: Research Disclosure, Item 22534, January 1983, published by Kenneth Mason Publications, Ltd., Emsworth, Hampshire P010 7DD, England; U.S. Pat. Nos. 4,439,520; 4,414,310; 4,433,048; 4,643,966; 4,647,528; 4,665,012; 4,672,027; 4,678,745; 4,693,964; 4,713,320; 4,722,886; 4,755,456; 4,775,617; 4,797,354; 4,801,522; 4,806,461; 4,835,095; 4,853,322; 4,914,014; 4,962,015; 4,985,350; 5,061,069 and 5,061,616.

The emulsions can be surface-sensitive emulsions, i.e., emulsions that form latent images primarily on the surfaces of the silver halide grains, or the emulsions can form internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent.

Photographic elements can be exposed to actinic radiation, typically in the visible region of the spectrum, to form a latent image and can then be processed to form a visible dye image. Processing to form a visible dye image includes the step of contacting the element with a color developing agent to reduce developable silver halide and oxidize the color developing agent. Oxidized color developing agent in turn reacts with the coupler to yield a dye.

With negative-working silver halide, the processing step described above provides a negative image. The described elements can be processed in the known C-41 color process as described in The British Journal of Photography Annual of 1988, pages 191–198. Where applicable, the element may be processed in accordance with color print processes such a the RA-4 process of Eastman Kodak Company as described in the British Journal of Photography Annual of 1988, Pp 198–199. To provide a positive (or reversal) image, the color development step can be preceded by development with a non-chromogenic developing agent to develop exposed silver halide, but not form dye, and followed by uniformly fogging the element to render unexposed silver halide developable. Alternatively, a direct positive emulsion can be employed to obtain a positive image.

Preferred color developing agents are p-phenylenediamines such as:

4-amino-N,N-diethylaniline hydrochloride, 4-amino-3-methyl-N,N-diethylaniline hydrochloride, 4-amino-3-methyl-N-ethyl-N-(β-(methanesulfonamido) ethyl)aniline sesquisulfate hydrate, 4-amino-3-methyl-N-ethyl-N-(β-hydroxyethyl)aniline sulfate, 4-amino-3-β-(methanesulfonamido)ethyl-N,N-diethylaniline hydrochloride and 4-amino-N-ethyl-N-(2-methoxyethyl)-m-toluidine di-p-toluene sulfonic acid.

Development is usually followed by the conventional steps of bleaching, fixing, or bleach-fixing, to remove silver or silver halide, washing, and drying.

The present invention also provides dyes of one of the general formulae:

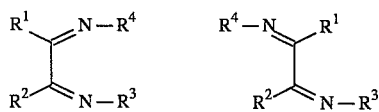

in which $R^1$, $R^2$ and $R^3$ are as defined above, and $R^4$ together with the N are the fragment of an oxidised color developing agent.

The couplers of formulae [1] and [2] may be prepared by the scheme described in Example 1 below.

The following Examples are included for a better understanding of the invention.

The present invention further provides photographic colour couplers as defined above as novel compounds.

EXAMPLE 2

Preparation of Coupler Compounds

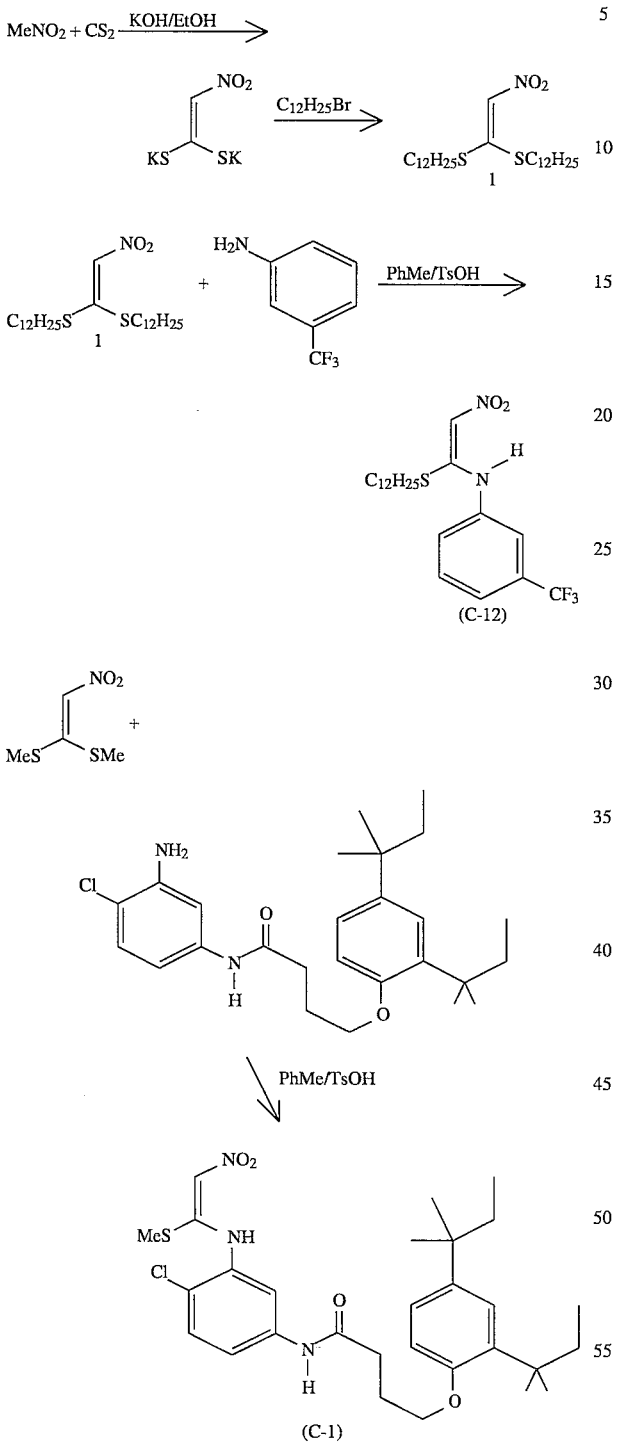

(C-1)

1. 1,1-Bis(n-dodecylthio)-2-nitroethylene

A solution of potassium hydroxide (119.83 g, 2.14 mol) in absolute ethanol (450 ml) was added dropwise over about 3 hours to a stirred solution of carbon disulphide (82.31 g, 1.08 mol) and nitromethane 60.82 g, 0.997 mol) in absolute ethanol (150 ml) at 35°–40° C. during which time an orange-brown solid separated. The mixture was allowed to cool and stand over the weekend. The solid was removed by filtration and recrystallised from ethanol/water. This dipotassium salt (135.01 g, 0.634 mol) was dissolved in water (200 ml). 1-Bromododecane (312.18 g, 1.25 mol) in dimethyl formamide (400 ml) was added to the orange-brown solution and the mixture heated to 100° C. with vigorous stirring. After 3 hours the mixture was cooled and left overnight. The oily suspension was added to water (4l) and extracted with diethyl ether (4×750 ml). The dark red organic solution was dried with magnesium sulphate and evaporated in vacuo to give an oil (238.1 g). This was purified by flash chromatography over silica eluting first with 60–80 petroleum ether and then with 19:1 60–80 petroleum ether/ethyl acetate to give the product (110.3 g, 0.233 mol, 37%) as an orange-yellow solid. All spectroscopic data is consistent with the proposed structure.

(C-12). 1-(n-Dodecylthio)-2-nitro-1-(N-(3-trifluoromethylanilino))ethylene

A mixture of 3-trifluoromethylaniline (3.24 g, 20.1 mmol), 1,1-bis(n-dodecylthio)-2-nitroethylene (1) (9.93 g, 21.0 mmol) and p-toluenesulphonic acid (150 mg) in toluene (150 ml) was heated at reflux overnight. The solvent was removed in vacuo and the residual oil (14.07 g) purified by column chromatography over silica using 5:1 60–80 petroleum ether/ethyl acetate as eluent to give the product (6.13 g, 14.2 mmol, 71%) as an oil. All spectroscopic data is consistent with the proposed structure.

(C-1). 1-(N-(2-chloro-5-(N-(4-(2,4-di(2-(2 -methylbutyl))phenoxy)-butyramido))anilino))-1 -methylthio-2-nitroethylene A mixture of 2-chloro-5-(N-(4-(2,4-di(2-(2 -methylbutyl))phenoxy)butyramido))aniline (30.27 g, 68.1 mmol) and 1,1-bis(methylthio)-2-nitroethylene (11.30 g, 68.5 mmol) was heated overnight in refluxing toluene (200 ml) containing p-toluenesulphonic acid (0.23 g). The mixture was allowed to cool and the solid removed by filtration. This solid was recrystallised from ethanol to give the product (12.37 g, 22.0 mmol, 34%) as a yellowish solid. All spectroscopic data is consistent with the proposed structure.

EXAMPLE 2

A dye from a representative example of the couplers of the invention was prepared as in the following scheme:

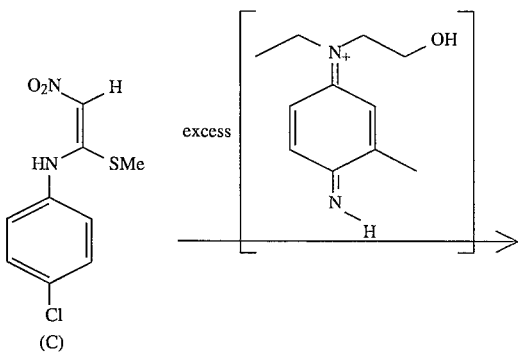

(C)

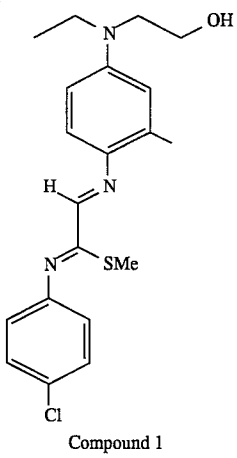

Compound 1

Compound 1

Excess developer was added with vigorous shaking to a biphasic mixture of C (1.01 g, 4.16 mmol) in ethyl acetate and an excess of potassium hydroxide and potassium persulphate in water. The organic layer was separated from the aqueous layer, washed with water, dried with magnesium sulphate and evaporated in vacuo to give a dark oil. This was purified by column chromatography over silica using 2:1 60–80 petroleum ether and ethyl acetate as eluent to give the product as a dark yellow oil (1.31 g) which crystallised upon standing. All spectroscopic data is consistent with the proposed structure.

EXAMPLE 3

Compounds of the present invention and control compounds A and B were incorporated into a photographic silver bromoiodide emulsion and coated in the following format:

| Gel Supercoat | Gelatin | 1.50 gm/m2 |
|---|---|---|
| | Silver bromoiodide | 0.81 gm/m2 |
| | Coupler | 1.932 mmol/m2 |
| Emulsion Layer | Gelatin | 2.42 gm/m2 |
| | Bis(vinylsulphonyl)-methane (hardener) | 0.06 gm/m2 |
| Support | | |

Control compound A had the following formula:

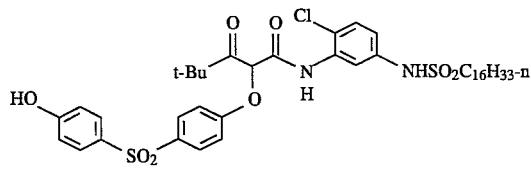

and control compound B had the following formula:

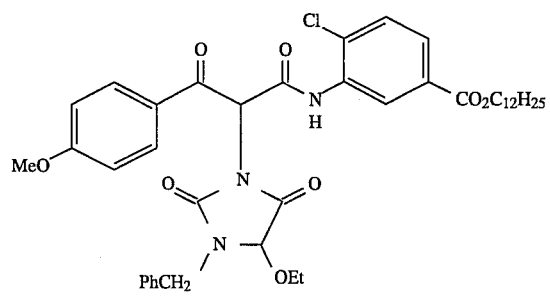

The coupler dispersion used contained 6% w/w gelatin, 9% coupler and coupler solvents in the ratio:-coupler: di-n-butyl phthalate:cyclohexanone 1.0:0.5:1.5 (w/w). The auxiliary solvent (cyclohexanone) was removed by washing the dispersion for 6 hours at 4° C. and pH 6.0.

(i) Sensitometric testing

The experimental photographic coatings prepared in this way were slit and chopped into 30 cm by 35 mm test strips. These were exposed (1.0 sec) through a 0–4.0 neutral density step wedge having 0.2 ND (Neutral Density) step increments and Daylight V, WRATTEN 35+38A filters and 0.3 ND filters then processed through a C-41 process as described in the British Journal of Photography (1988) 196–198 using the following process times:

| Developer | 2.5 minutes |
|---|---|
| Bleach | 4.0 minutes |
| Wash | 2.0 minutes |
| Fix | 4.0 minutes |
| Wash | 2.0 minutes |

For each test strip, step-wedge densities were measured using a spectral array automatic transmission densitometer. Measurements of sensitometric parameters were obtained from the DlogE curves.

(ii) Spectrophotometric testing 35 mm Test strips were exposed as above through a 0–0.9 ND step-wedge (0.3 ND steps) test object and Daylight V, WRATTEN 35+38A filters and the correct ND filters to give an optical density of circa 1.0. The strips were processed using the standard conditions described above and samples cut from the yellow dye image step with density closest to 1.0. Visible absorption spectra (normalised to 1.0 density) were obtained using a PYE UNICAM SP8-100 spectrophotometer. The amount of unwanted green absorption (measured at 525 nm) relative to the main absorption peak is given by:

$$\text{Unwanted green absorption (at 525 nm)} = \frac{\text{density at 525 nm}}{\text{density at wavelength of maximum absorption}}$$

(iii) Measurement of continued coupling in the bleach

Two sets of 35 mm strips were exposed as in (i) for 1.0 sec through a 0–4.0 ND step-wedge (0.2 ND increments) and Daylight V, Wratten 35+38A filters and 0.3 ND filters. One set of strips was processed through a modified C-41 process, in which the pH of the bleach was raised to 5.5 by the addition of 0.880 ammonia, using the following processing sequence:

| | |
|---|---|
| Developer | 2.5 minutes |
| Modified Bleach | 4.0 minutes |
| Wash | 2.0 minutes |
| Fix | 4.0 minutes |
| Wash | 2.0 minutes |

The second set of 35 mm test strips was processed through the following sequence, containing the modified bleach (pH5.5) as described above with a stopbath (1% acetic acid solution) and wash step inserted between the developer and bleach steps:

| | |
|---|---|
| Developer | 2.5 minutes |
| Stopbath | 1.0 minute |
| Wash | 2.0 minutes |
| Modified Bleach | 4.0 minutes |
| Wash | 2.0 minutes |
| Fix | 4.0 minutes |
| Wash | 2.0 minutes |

For the test strips processed through each of the above sequences, step-wedge densities were measured using a spectral array automatic transmission densitometer. Measurements of minimum density (Dmin) were obtained from the DlogE curves. The non-imagewise stain due to continued coupling in the bleach (Dmin) was calculated for each compound by subtracting the Dmin for the test strip processed through the stopbath process from the Dmin for the test strip processed through the process omitting the stopbath step:

$$\Delta Dmin = Dmin(\text{no stopbath process}) - Dmin(\text{process with stopbath}).$$

Figure 2:
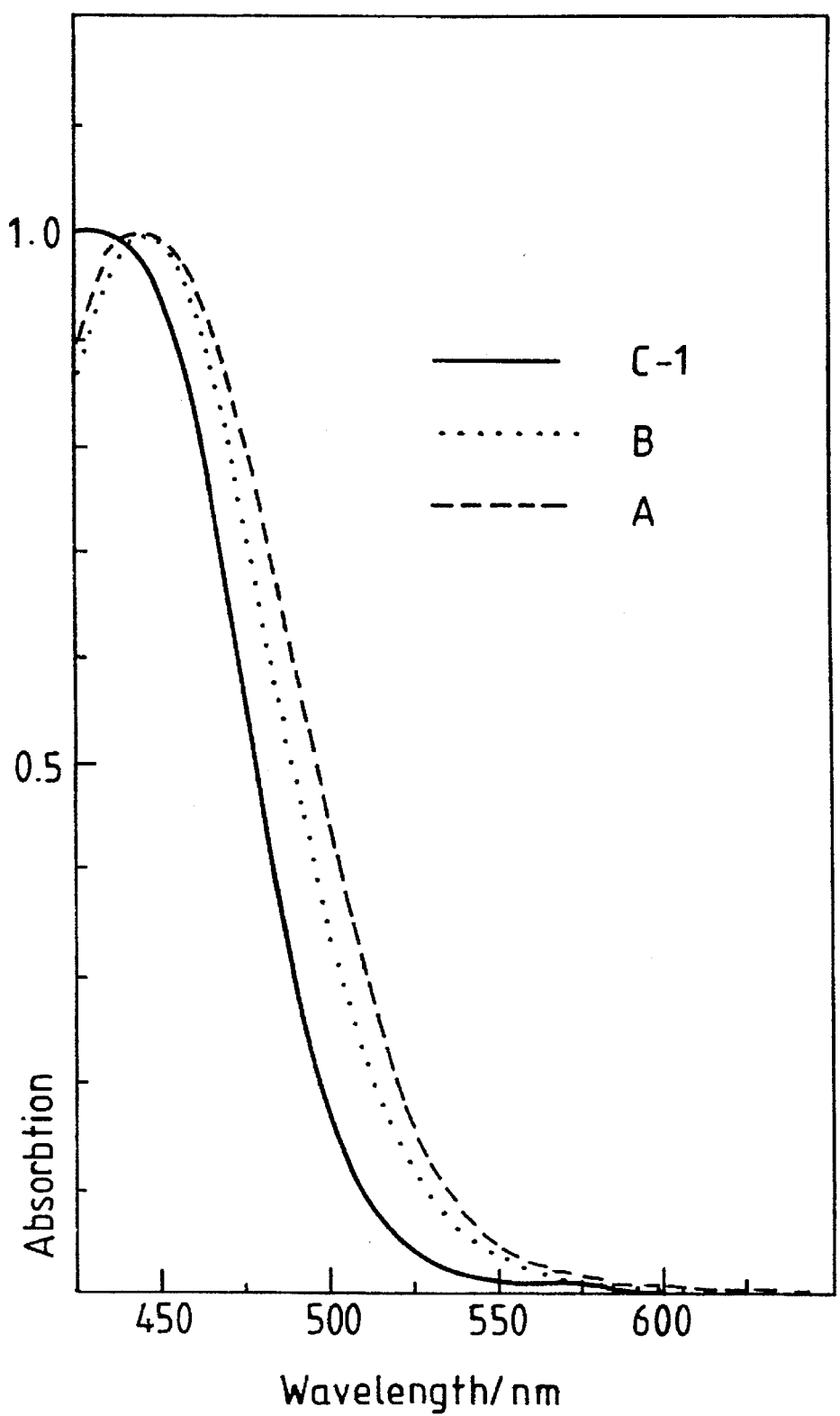

The visible absorption spectra of (C-12) and (C-1) are shown in FIGS. 1 and 2 respectively.

The results are shown below:

| Compound | Unwanted Green Absorption at 525 nm | Continued coupling (ΔDmin) |
|---|---|---|
| A | 0.16 | 0.01 |
| B | 0.12 | 0.07 |
| C-1 | 0.03 | 0.01 |
| C-12 | 0.05 | 0.00 |

It can be seen that the couplers of the invention (C-1 and C-12) have less unwanted absorption in the green and display less continued coupling than prior art coupler (B).

What is claimed is:

1. A photographic element comprising a support, at least one photosensitive silver halide layer and in or adjacent said silver halide layer a yellow dye-forming color coupler of one of the general formulas:

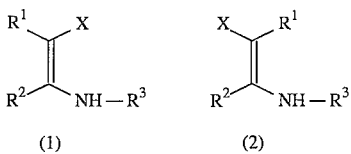

wherein $R^1$ is a group substantially without any electron-withdrawing capability, $R^2$ is a substituent not incompatible with the function of the compound, $R^3$ is an alkyl, aryl or heterocyclic group any of which may be substituted, provided that $R^1$ and $R^2$ or $R^1$ and $R^3$ may not together form a cyclic group, and X is a coupling-off group.

2. A photographic element as claimed in claim 1 in which the coupling-off group X is a nitro group.

3. A photographic element as claimed in claim 1 in which $R^1$ is hydrogen, a substituted or unsubstituted aliphatic, a substituted or unsubstituted aryl, or a substituted or unsubstituted heterocyclic group.

4. A photographic element as claimed in claim 1 in which $R^2$ is hydrogen, halogen, nitro, cyano, or substituted or unsubstituted thioalkyl, thioaryl, alkyl, aryl, heterocyclic, carbonamido, alkyloxy, aryloxy, alkyloxycarbonyl, alkylsulphoxyl, arylsulphoxyl, alkylsulphonyl, arylsulphonyl, amino, or a phosphorus atom substituted with a hydrocarbon group or an acyl group.

5. A photographic element as claimed in claim 1 in which $R^3$ is a substituted or unsubstituted aryl, substituted or unsubstituted heterocyclic, or an acyl group.

6. A photographic element as claimed in claim 1 in which the coupler contains a ballast group of such size and configuration that the coupler is non-diffusible in photographic layers.

7. A photographic element as claimed in claim 1 in which the material is a multicolor photographic material comprising a support bearing a yellow dye image-forming unit comprised of at least one blue-sensitive silver halide emulsion layer having associated therewith at least one yellow dye-forming coupler, at least one magenta dye image-forming unit comprising at least one green-sensitive silver halide emulsion layer having associated therewith at least one magenta dye-forming coupler at least one cyan dye image-forming unit comprising at least one red-sensitive silver halide emulsion layer having associated therewith at least one cyan dye-forming coupler.

8. A process for forming an image in an element as described in claim 1 after said element has been exposed to light comprising contacting said element with a color developing agent.

9. The process of claim 8 wherein said exposed element is subjected to a reversal color development process.

* * * * *